United States Patent
Everson et al.

(10) Patent No.: US 12,007,383 B2
(45) Date of Patent: *Jun. 11, 2024

(54) METHOD FOR ASSESSMENT OF HEPATIC FUNCTION AND PORTAL BLOOD FLOW

(71) Applicant: The Regents of the University of Colorado, Denver, CO (US)

(72) Inventors: Gregory Thomas Everson, Englewood, CO (US); Steve Mark Helmke, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 388 days.

This patent is subject to a terminal disclaimer.

(21) Appl. No.: 16/878,510

(22) Filed: May 19, 2020

(65) Prior Publication Data

US 2020/0333323 A1    Oct. 22, 2020

Related U.S. Application Data

(60) Continuation of application No. 16/246,174, filed on Jan. 11, 2019, now Pat. No. 10,697,956, which is a (Continued)

(51) Int. Cl.
*G01N 33/49* (2006.01)
*A61J 1/05* (2006.01)
*G01N 33/92* (2006.01)

(52) U.S. Cl.
CPC ............... *G01N 33/49* (2013.01); *A61J 1/05* (2013.01); *G01N 33/92* (2013.01); *G01N 2800/085* (2013.01); *Y02A 90/10* (2018.01)

(58) Field of Classification Search
CPC .. G01N 33/49; G01N 33/92; G01N 2800/085; A61J 1/05; Y02A 90/10
See application file for complete search history.

(56) References Cited

U.S. PATENT DOCUMENTS

| 4,207,308 A | 6/1980 | Spenney |
| 6,778,269 B2 | 8/2004 | Fink et al. |

(Continued)

FOREIGN PATENT DOCUMENTS

| AU | 2012262329 | 10/2014 |
| EP | 1150123 | 10/2001 |

(Continued)

OTHER PUBLICATIONS

Laharie et al., J of Hepatology, 2010, 53:1035-1040.*

(Continued)

*Primary Examiner* — Sean C. Barron
(74) *Attorney, Agent, or Firm* — Merchant & Gould P.C.

(57) ABSTRACT

A method for estimating portal blood flow and hepatic function in a subject is provided. In one example, the STAT test is an in vitro simplified, convenient test intended for screening purposes that can reasonably estimate the portal blood flow from a single blood sample taken 60 minutes after orally administered deuterated-cholate. The test can be administered to a patient having, or suspected of having, Chronic Hepatitis C, Primary Sclerosing Cholangitis (PSC), Non-Alcoholic Fatty Liver Disease (NAFLD), or any chronic liver disease.

21 Claims, 11 Drawing Sheets

Related U.S. Application Data continuation of application No. 15/263,020, filed on Sep. 12, 2016, now Pat. No. 10,222,366, which is a continuation of application No. 14/597,986, filed on Jan. 15, 2015, now abandoned, which is a division of application No. 13/484,083, filed on May 30, 2012, now Pat. No. 8,961,925.

(60) Provisional application No. 61/491,429, filed on May 31, 2011.

(56) References Cited

U.S. PATENT DOCUMENTS

| | | |
|---|---|---|
| 7,060,250 B2 | 6/2006 | McMurry et al. |
| 8,613,904 B2 | 12/2013 | Everson et al. |
| 8,778,299 B2 | 7/2014 | Everson |
| 8,961,925 B2 | 2/2015 | Everson et al. |
| 9,091,701 B2 | 7/2015 | Everson et al. |
| 9,417,230 B2 | 8/2016 | Everson |
| 9,639,665 B2 | 5/2017 | Everson et al. |
| 9,759,731 B2 | 9/2017 | Everson et al. |
| 10,222,366 B2 | 3/2019 | Everson et al. |
| 10,697,956 B2 | 6/2020 | Everson et al. |
| 2006/0067881 A1 | 3/2006 | Groman et al. |
| 2006/0251576 A1 | 11/2006 | Hellerstein |
| 2008/0279766 A1 | 11/2008 | Everson et al. |
| 2010/0055734 A1 | 3/2010 | Everson |
| 2012/0329161 A1 | 12/2012 | Everson et al. |
| 2014/0067276 A1 | 3/2014 | Everson et al. |
| 2014/0147875 A1 | 5/2014 | Everson et al. |
| 2014/0326926 A1 | 11/2014 | Everson et al. |
| 2015/0204842 A1 | 7/2015 | Everson et al. |
| 2015/0268255 A1 | 9/2015 | Everson et al. |
| 2016/0305930 A1 | 10/2016 | Everson et al. |

FOREIGN PATENT DOCUMENTS

| | | |
|---|---|---|
| JP | 2003532899 | 11/2003 |
| JP | 2004507740 | 3/2004 |
| JP | 2010502979 | 1/2010 |
| WO | 02/16949 | 2/2002 |
| WO | 2008/029145 | 3/2008 |
| WO | 2012/166802 | 12/2012 |
| WO | 2014/075082 | 5/2014 |

OTHER PUBLICATIONS

Whiting-O'Keefe et al. Methotrexate and histologic hepatic abnormalities: ameta-analysis. Am J Med (1991), 90(6), 711-716, Abstract Only. (Year: 1991).*

Chronic Hepatitis Data Sheet, Merck, Sharp & Dohme, Corp., 1 page (2010-2011).

Dax et al., "HPLC-Continuous-Flow Fast Atom Bombardment Mass Spectrometry (HPLC-CFFAB)—a Convenient Method for the Analysis of Bile Acids in Bile and Serum"; Chromatographia, 40(11/12):674-679 (Jun. 1995).

Decompensated Cirrhosis Data Sheet, U.S. Department of Veterans Affairs, 1 page (2011).

Denaro et al., "The effect of liver disease on urine caffeine metabolite ratios"; Clinical Pharmacology and Therapeutics, 59:624-635 (1996).

Di Bisceglie, "Prolonged therapy of advanced chronic hepatitis C with low-dose peginterferon"; N Engl J Med, 359(23):2429-2441 (Dec. 4, 2008).

Everson et al., "Quantitative Tests (QLFTS) Detect Impaired Hepatic Function in a High Proportion of Chronic Hepatitis C Patients With Fibrosis or Compensated Cirrhosis and may Predict Risk of Cirrhosis, Splenomegaly, and Varices"; Hepatology, 38:304-305 (Jan. 1, 2003).

Everson et al., "Portal-systemic shunting in patients with fibrosis or cirrhosis due to chronic hepatitis C: the minimal model for measuring cholate clearances and shunt", Alimentary Pharmacology & Therapeutics, 26:401-410 (2007).

Everson et al., "The spectrum of hepatic functional impairment in compensated chronic hepatitis C: results from the Hepatitis C Anti-viral Long-term Treatment against Cirrhosis Trial"; Alimentary Pharmacology & Therapeutics, 27:798-809 (2008).

Everson et al. "Quantitative tests of liver function measure hepatic improvement after sustained virological response: results from the HALT-C trial"; Alimentary Pharmacology & Therapeutics, 29:589-601(2009).

Everson et al., "Hepatic Impairment Measured by Quantitative Tests of Liver Function (QLFTs) Predicts Clinical Outcome in Patients with Advanced Fibrosis: Results from the Hepatitis C Anti-viral Long-term Treatment against Cirrhosis (HALT-C) trial"; Hepatology 50(4 Suppl.):1057A, Abstract 1627 (2009).

Everson et al., "Quantitative Liver Function Tests Improve the Prediction of Clinical Outcomes in Chronic Hepatitis C: Results from the Hepatitis C Antiviral Long-term Treatment Against Cirrhosis Trial"; Hepatology, 55(4):1019-1029 (Apr. 2012).

Examination Report No. 1 from related Australian patent application 2012262329, dated Jun. 23, 2014.

Extended European Search Report for EP 06734026.5, dated Mar. 31, 2011.

European Search Report for Application No. 10815965.8 dated Apr. 17, 2013.

Gilmore et al., "Plasma clearance of oral and intravenous cholic acid in subjects with and without chronic liver disease"; Gut, 21:123-127 (1980).

Golden et al., "Application of an enzyme-multiplied immunoassay technique for determination of caffeine elimination kinetics as a test of liver function in clinically normal dogs"; American Journal of Veterinary Research, 55(6):790-794 (Jun. 1994).

Guidance for Industry, Bioanalytical Method Validation, (May 2001).

Haque et al., "Hepatitis C antiviral long-term treatment against cirrhosis (HALT-C) trial"; Annals of Hepatology, 8(1):78-79 (Jan.-Mar. 2009).

Hechey et al., "Syntheses with stable isotopes: synthesis of deuterium and 13C labeled bile acids," Journal of Labelled Compounds, IX(4):703-719 (Oct.-Dec. 1973).

Helmke et al., "Slow, Moderate, and Rapid Progressors: Three Distinct Categories of Patients with Primary Sclerosing Cholangitis Detected by Functional Assessment using Cholate Testing," Hepatology, 56(4)(Suppl):1133A, Abstract No. 2027 (Oct. 2012).

Hoofnagle, "Course and outcome of hepatitis C"; Hepatology, 36(5):S21 (Nov. 2002).

Hydzik et al., "Usefulness of 13C-methacetin breath test in liver function testing in Amanita phalloides poisoning: breast feeding woman case"; Clinical Toxicology, 46:1077-1082 (2008).

International Search Report for PCT/US06/03132, dated Jul. 11, 2007.

International Search Report and Written Opinion for PCT/US10/47676, dated Feb. 2, 2011.

Invitation to Pay Additional Fees for PCT/US10/47676, dated Nov. 17, 2010.

International Search Report and Written Opinion cited in PCT/US2012/040008 dated Sep. 6, 2012.

International Search Report and Written Opinion for PCT/US13/69708 dated Feb. 10, 2014.

Kamath et al., "A Model to Predict Survival in Patients with End-Stage Liver Disease"; Hepatology, 33(2):464-470 (Feb. 2001).

Koster et al., "Recent Developments in On-line SPE for HPLC and LC-MS in Bioanalysis"; Guide to LC-MS, 3 pp. (Dec. 2001).

Krumbiegel et al., "[15N]methacetin urine test: a method to study the development of hepatic detoxification capacity"; Eur J Pediatr., 149(6):393-395 (Mar. 1990).

Lalazar et al., "A continuous 13C methacetin breath test for non-invasive assessment of intrahepatic inflammation and fibrosis in patients with chronic HCV infection and normal ALT"; Journal of Viral Hepatitis 15(10):716-28 (Oct. 2008).

Martucci, "Deconvolutional Analysis on Clearance Curves of Simultaneously Administered Oral and Intravenous Doses of 2,2,4,4-2H Cholate and 24-13C Cholate: Minimal Model to Determine First-

(56) References Cited

OTHER PUBLICATIONS

Pass Hepatic Extraction of Cholate in Humans"; Research paper, University of Colorado Health Sciences Center (Aug. 2004).
Medrzejewski et al., "Plasma Clearance of Cholic Acid in Patients With Chronic Diseases of the Liver"; Polski Tygodnik Lekarski, 45(16-18):335-337, Abstract Only, 1 page. (Apr. 16-30, 1990).
Everson et al., "Qualitative Tests (QLFTS) Detect Impaired Hepatic Function in a High Proportion of Patients with Chronic HCV and Firbrosis or Cirrhosis and May Predict Risk of Cirrhosis, Splenomegaly and Varices", presentation at the 54th Annual Meeting of the American Association for the Stady of Liver Diseases, (Oct. 2003).
Queiroz et al., "Renal sodium retention complicating alcoholic liver disease: relation to portosystemic shunting and liver function", LCGC North America 22(10) (Oct. 2004).
Rector et al., Renal sodium retention complicating alcoholic liver disease: Relation to portosystemic shunting and liver function Hepatology 12(3):455-459 (1990).
Renner et al., "Caffeine: A Model Compound for Measuring Liver Function", Hepatology 4(1):38-46 (1984).
Shrestha et al., "Quantitative liver function tests define the functional severity of liver disease in early-state cirrhosis"; Liver Transplantation and Surgery 3(2):166-167, 172 (Mar. 1997).
Stellaard, et al., "Simultaneous determination of cholic acid and chenodeoxycholic acid pool size and fractional turnover rates in human serum using 13C-labeled bile acids"; Journal of Lipid Research, 25:1313-1319 (1984).
Afdhal et al., "Advances in Hepatology—Fibroscan (Transient Elastography) for the Measurement of Liver Fibrosis"; Sec. Ed. Schiff, Gastroenterology & Hepatology; 8(9):605-607 (Sep. 2012).
Bio Predictive, "Technical Recommendations for FibroTest and FibroMax assays"; A Guide for biologists and laboratories, V. 1.17, 28 pgs (Oct. 20, 2014).
DeMark, "A method for the accurate measurement of isotope ratios of chenodeoxycholic and cholic acids in serum"; J Lipid Res, 23:204-210 (1982).
Eichelbaum, "Simultaneous Determination of the intravenous and Oral Pharmacokinetic Parameters of D,L-Verapamil Using Stable Isotope-Labelled Verapamil"; Eur J Clin Pharmacol, 19:133-137 (1981).
Everson et al., "Functional Elements Associated with Hepatic Regeneration in Living Donors After Right Hepatic Lobectomy," Liver Transplantation, vol. 19, No. pp. 292-304 (2013).
Exalenz Breathid® breath test device for the diagnosis of liver disease; Health Policy Advisory Committee on Technology—Technology Brief (Aug. 2012). Copy can be obtained from: http://www.health.qld.gov.au/healthpact.
HCV Fibrosure™, Informational Sheet; Laboratory Corporation of America (2004).
Helmke et al., "Noninvasive assessment of liver function"; Liver—Current Opinion in Gastroenterology 31(3):1-10 (Feb. 31, 2015).
Herold et al., "Quantitative testing of liver function in patients with cirrhosis due to chronic hepatitis C to assess disease severity"; Liver, 21:26-30 (2001).
Kern, "Normal Plasma Cholesterol in an 88-year-old Man Who Eats 25 Eggs a Day"; New England J Medicine, 324:896-899 (1991).
Nguyen et al., "Diagnostic and Therapeutic Advances in Hepatology—Noninvasive Assessment of Liver Fibrosis"; Hepatology; 2107-2110 (Jun. 2011).
Ratziu et al., "Diagnostic value of biochemical markers (Fibro Test-FibroSURE) for the prediction of liver fibrosis in patients with non-alcoholic fatty liver disease"; BMC Gastroenterology; 6:6 (Feb. 14, 2006).
Shah et al., "Comparison of Noninvasive Markers of Fibrosis in Patients With Nonalcoholic Fatty Liver Disease"; Clinical Gastroenterology and Hepatology; 7(10):1104-1112 (2009).
Supplementary European Search Report for Application No. 13853943.2 dated May 23, 2016, 8 pages total.
Wallack et al., "Non-invasive measurement of the portal circulation using cholates quantifies disease severity in primary sclerosing cholangitis", Gastroenterology, vol. 142, No. 5, suppl. 1, p. S911 (May 1, 2012).
Miescher et al., "Portal-systemic spill-over of bile acids: a study of mechanisms using ursodeoxycholic acid"; European J of Clinical Investigation; 13:439-445 (1983).
Stellaard, et al., "Measurement of Bile Acid Kinetics in Human Serum Using Stable Isotope Labeled Chenodeoxycholic Acid and Capillary Gas Chromatograpy Electron Impact Mass Spectrometry," Biomedical Mass Spectrometry, 10(3):187-191 (1983).
Stellaard, "Simultaneous determination of pool sizes and fractional turnover rates, of deoxycholic acid, cholic acid and chenodeoxycholic acid in man by isotope dilution with 2H and 13C labels and serum sampling," Biomedical and Environmental Mass Spectrometry, vol. 14, pp. 609-611 (1987).
Office Action for EP 12731209.8 dated Sep. 7, 2016, 4 pages total.
Examination Report for Australian Application No. 2013341378, dated Jan. 17, 2017, 3 pages total.
Japanese Office Action dated Aug. 28, 2017 in Japanese patent application No. 2015-542017 and English language translation, 8 pages total.
Matern et al., "Oral cholate tolerance test—an application of specific radio immunoassays for the determination of serum-conjugated cholic and deoxycholic acids", Bile Acid Metabolism in Health and Disease, 253-261 (1980).
Extended European Search Report for EP Application No. 20159648.3 dated May 15, 2020, 9 pages total.
Angulo et al., 2007, The NAFLD fibrosis score: A noninvasive system that identifies liver fibrosis in patients with NAFLD. Hepatology. 45: 846-854.
Wong et al., 2010, Diagnosis of fibrosis and cirrhosis using liver stiffness measurement in nonalcoholic fatty liver disease. Hepatology. 51: 454-462.

* cited by examiner

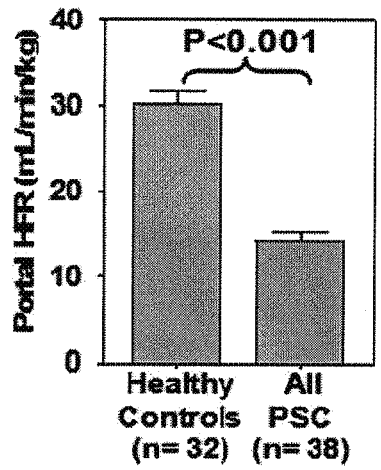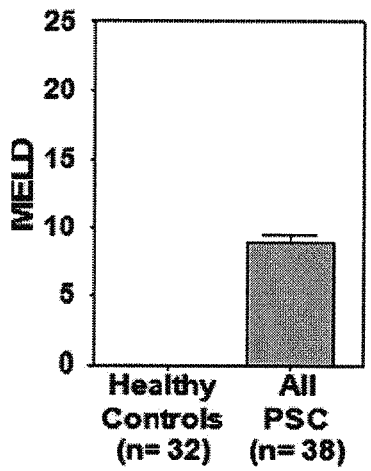
FIGURE 10A  FIGURE 10B
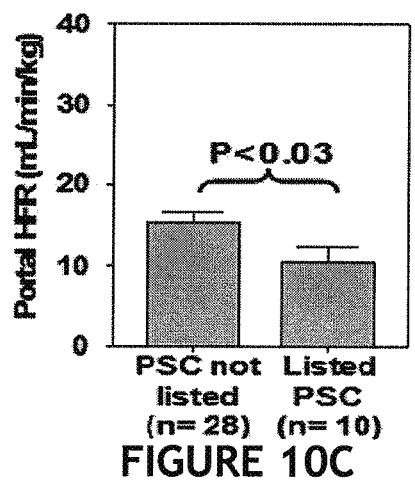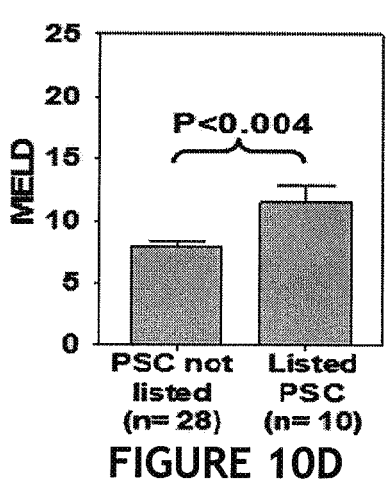
FIGURE 10C  FIGURE 10D
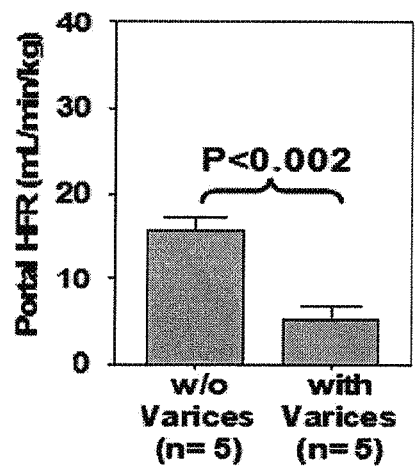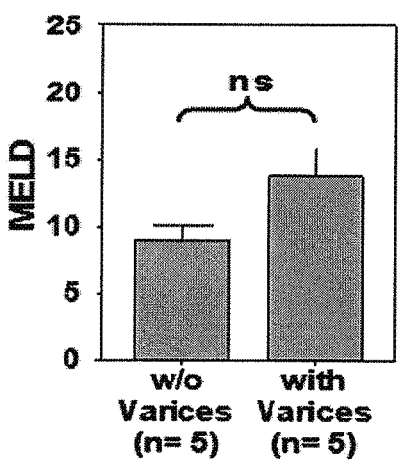
FIGURE 10E  FIGURE 10F

METHOD FOR ASSESSMENT OF HEPATIC FUNCTION AND PORTAL BLOOD FLOW

RELATED APPLICATIONS

This application is a continuation of U.S. application Ser. No. 16/246,176 filed Jan. 11, 2019, issued as U.S. Pat. No. 10,697,956 on Jun. 30, 2020, which is a continuation of U.S. application Ser. No. 15/263,020, filed Sep. 12, 2016, issued as U.S. Pat. No. 10,222,366 of on Mar. 5, 2019, which is a continuation of US Application Ser. No. 14/597,986, filed Jan. 15, 2015, now abandoned, which is a divisional of U.S. application Ser. No. 13/484,083, filed May 30, 2012, issued as U.S. Pat. No. 8,961,925 on Feb. 24, 2015, which claims the benefit of U.S. Provisional Application Ser. No. 61/491,42.9, filed May 31, 2011, the entire contents of each of which are incorporated herein by reference.

STATEMENT REGARDING FEDERALLY SPONSORED RESEARCH OR DEVELOPMENT

This invention was made with government support under grant numbers Contract No. DK092327 and RR000051 awarded by the National Institutes of Health. The government has certain rights in this invention.

BACKGROUND OF THE INVENTION

All liver diseases have common pathophysiologic characteristics with disease progression fueled by inflammation, accumulation of fibrosis, and alteration of the portal circulation. There are difficulties in monitoring hepatic function and portal blood flow in patients with liver disease. Such diseases include chronic hepatitis C, nonalcoholic fatty liver disease (NAFLD), primary sclerosing cholangitis (PSC), chronic hepatitis B, alcoholic liver disease, autoimmune liver disease, cryptogenic cirrhosis, hemochromatosis, Wilson's disease, alpha-1-antitrypsin deficiency, and cholestatic liver diseases.

Chronic hepatitis C. Two known liver function tests can be used to measure portal blood flow and were previously validated using a large cohort of patients with chronic hepatitis C. One such liver function test, called the FLOW test, accurately measures the portal blood flow from a minimum of 5 blood samples taken over a period of 90 minutes after an oral dose of deuterated-cholate. The FLOW test is disclosed in Everson, US 2010/0055734, Methods for Diagnosis and Intervention of Hepatic Disorders, filed Sep. 11, 2009, which is incorporated herein by reference. Another liver function test, the SHUNT test, comprises simultaneous administration of an intravenous dose of $^{13}$C-cholate and an oral dose of deuterated-cholate. The SHUNT test can be used to measure portal blood flow, and systemic hepatic blood flow and therefore determine the amount of portal-systemic shunting. The SHUNT test is disclosed in Everson et al., US2008/0279766, Methods for Diagnosis and Intervention of Hepatic Disorders, filed Jan. 26, 2006, which is incorporated herein by reference. A test that could more simply and rapidly estimate portal blood flow and hepatic function in patients with chronic hepatic C is desirable. A simple, efficient test for estimating portal blood flow is also applicable to other chronic liver diseases.

Nonalcoholic Fatty Liver Disease. Non-Alcoholic Fatty Liver Disease (NAFLD) (Browning et al., 2004, Prevalence of hepatic steatosis in an urban population in the united states: Impact of ethnicity. Hepatology. 40: 1387-1395) may affect up to one-third of the US population and this vast epidemic is mostly hidden because people are usually asymptomatic and have normal 'liver function tests'. The prevalence continues to rise along with the major risk factors which are obesity, metabolic syndrome, and insulin resistance. NAFLD can progress from simple fatty liver called steatosis, which is relatively benign, to the more serious NASH, Non-Alcoholic SteatoHepatitis. Hepatitis is inflammation of the liver and can also be caused by excessive drinking, as in Alcoholic SteatoHepatitis (ASH), or viral infection, i.e., Chronic Hepatitis C (CHC). All these chronic liver diseases (CLDs) are characterized by a similar pathophysiology with inflammation, cell death, and fibrosis leading to a progressive disruption of the hepatic microvasculature. About 5% of NAFLD patients will progress to cirrhosis (Adams et al., 2005, The natural history of nonalcoholic fatty liver disease: A population-based cohort study. Gastroenterology. 129: 113-121) and NAFLD will surpass CHC as the leading indication for liver transplantation.

Primary Sclerosing Cholangitis

The hallmark of PSC pathophysiology is portal fibrosis leading to portal hypertension (PHTN) earlier in disease compared to other etiologies of liver disease. The assessment of disease severity in PSC lacks a gold standard, as liver biopsy has significant sampling error and is no longer recommended. Hepatic Venous Pressure Gradient (HVPG) is invasive, expensive and impractical, and clinical models were really created to assess late-stage disease. There is an unmet need for accurate non-invasive assessment of PSC over the spectrum of disease severity.

Chronic liver disease. Although chronic hepatitis C and NAFLD are the two most common chronic liver diseases in the US, a screening test for estimation of portal blood flow is desirable for patients having, or suspected of having, any chronic liver disease, such as, but not limited to, chronic hepatitis C, nonalcoholic fatty liver disease (NAFLD), chronic hepatitis B, primary sclerosing cholangitis (PSC), alcoholic liver disease, non-alcoholic steatohepatitis (NASH), autoimmune liver disease, cryptogenic cirrhosis, hemochromatosis, Wilson's disease, alpha-1-antitrypsin deficiency, and cholestatic liver diseases. Estimates suggest that 30 million or more Americans may be affected by chronic liver disease.

Difficulties in Monitoring Patients with Chronic Liver Disease. Currently the only way to distinguish Non-Alcoholic SteatoHepatitis (NASH) from steatosis and to monitor NASH progression is through a needle biopsy, which assesses the grade of inflammatory activity and the stage of fibrosis. Biopsy is considered the gold standard despite suffering from numerous sources of inaccuracy and the risks of an invasive procedure. Patients must be sedated and a portion will experience bleeding and other complications (Janes and Lindor, 1993, Ann Intern Med. 118: 96-98; Seeff et al., 2010, Clin Gastroenterol Hepatol. 8: 877-883). The needle biopsy is a very small specimen of a very large organ and it is very difficult to obtain large enough pieces from enough locations for adequate sampling (Vuppalanchi et al., 2009, Clin Gastroenterol Hepatol. 7: 481-486; Bedossa et al., 2003, Hepatology. 38: 1449-1457; Regev et al., 2002, Am J Gastroenterol. 97: 2614-2618). Biopsy interpretation is subjective and depends on the expertise of the observer (Rousselet et al., 2005, Hepatology. 41: 257-264) and the size and number of tissue samples (Rousselet et al., 2005; Vuppalanchi et al., 2009). In describing the progression of fibrosis in CHC the 6 stage Ishak system (Ishak et al., 1995, J Hepatol. 22: 696-699) may be used, but more typical is a simpler 4 stage system (Knodell et al., 1981, Hepatology. 1: 431-435; Batts and Ludwig, 1995, Am J Surg Pathol. 19: 1409-1417; Scheuer, 1991, J Hepatol. 13: 372-374) such as Metavir (Group, TFMCS, 1994, Hepatology. 20: 15-20) which is very comparable to the 4 stage system used for NASH (Brunt et al., 1999, Am J Gastroenterol. 94: 2467-2474; Kleiner et al., 2005. Hepatology 41: 1313-1321). However, the heterogeneity of lesions in NASH decreases the accuracy (Ratziu et al., 2005, Gastroenterology. 128: 1898-1906). It is not practical to biopsy a third of the population especially since the method has an estimated error rate of 20% or greater. Other standard liver blood tests are not very useful. Liver enzymes such as ALT or AST may spike during activity flares, but often they are in the normal range due to the slow rate of progression. The liver's production of albumin or clotting factors only declines at the latest stages of CLD. Noninvasive means to distinguish NASH from steatosis and accurately monitor NASH progression are desirable.

Deficiencies of Other Non-invasive Test Methods. The need for non-invasive liver assessment has led to the commercialization of new methods including biomarker panels, metabolic breath tests, and transient elastography. Biomarker panels (Mukherjee and Sorrell, 2006, Noninvasive tests for liver fibrosis. Semin Liver Dis. 26: 337-347; Shah et al., 2009, Comparison of noninvasive markers of fibrosis in patients with nonalcoholic fatty live disease. Clin Gastroenterol Hepatol. 7: 1104-1112) such as FIBROTEST® are not sensitive enough to detect either early stage CHC (Boursier et al., 2009. Improved diagnostic accuracy of blood tests for severe fibrosis and cirrhosis in chronic hepatitis c. Eur J Gastroenterol Hepatol. 21: 28-38; Shaheen et al., 2007, FIBROTEST and FIBROSCAN for the prediction of hepatitis c-related fibrosis: A systematic review of diagnostic test accuracy. Am J Gastroenterol. 102: 2589-2600) or NASH (Ratziu et al., 2006, Diagnostic value of biochemical markers (FIBROTEST-FIBROSURE) for the prediction of liver fibrosis in patients with non-alcoholic fatty liver disease. BMC Gastroenterol. 6: 6; Angulo et al., 2007, The NAFLD fibrosis score: A noninvasive system that identifies liver fibrosis in patients with NAFLD. Hepatology. 45: 846-854; Wong et al., 2010, Diagnosis of fibrosis and cirrhosis using liver stiffness measurement in nonalcoholic fatty liver disease. Hepatology. 51: 454-462) or to track progression because circulating proteins/fragments can't report accurately on fine structure, the disruption of the microvasculature, and impairment of flow.

Metabolic tests are variable because they rely on CYP enzymes which vary according to gender, age, genetics, diet, medications and they are insensitive to early stage disease because the enzymes do not significantly decline until later stages. BREATHID® has a methacetin metabolic test in FDA trials, but this method failed to detect early stage CHC in earlier studies (Braden et al., 2005. 13c-methacetin breath test as liver function test in patients with chronic hepatitis c virus infection. Aliment Pharmacol Ther. 21: 179-.185).

FIBROSCAN®, also in FDA trials, uses transient elastography to measure liver stiffness to estimate fibrosis (Del Poggio and Colombo, 2009, Is transient elastography a useful tool for screening liver disease? World J Gastroenterol. 15: 1409-1414). This method is insensitive to early stage CID (Del Poggio and Colombo, 2009, infra; Friedrich-Rust et al., 2008. Performance of transient elastography for the staging of liver fibrosis: A meta-analysis. Gastroenterology. 134: 960-974) including CHC (Shaheen et al., 2007, infra, and Rossi et al., 2003. Validation of the fibrotest biochemical markers score in assessing liver fibrosis in hepatitis c patients. Clin Chem. 49: 450-454) or NASH (Wong et al., 2010, Diagnosis of fibrosis and cirrhosis using liver stiffness measurement in nonalcoholic fatty liver disease. Hepatology. 51: 454-462) and is compromised by obesity, a major risk factor for NAFLD. More effective noninvasive means to distinguish NASH from steatosis and accurately monitor NASH progression are clearly needed.

A method for estimating portal blood flow and hepatic function in a subject is provided. The herein disclosed single-point STAT test is a simplified, convenient test intended for screening purposes that can reasonably estimate the portal blood flow from a single blood sample taken at, e.g., 60 minutes after orally administered deuterated-cholate. All liver diseases have common pathophysiologic characteristics with disease progression fueled by inflammation, accumulation of fibrosis, and alteration of the portal circulation. Because STAT provides an accurate estimate of portal blood flow, the test is developed as a diagnostic with application for all liver diseases. Liver diseases for which the STAT diagnostic could be utilized include, but are not limited to, chronic hepatitis C, nonalcoholic fatty liver disease (NAFLD), primary sclerosing cholangitis (PSC), chronic hepatitis B, alcoholic liver disease, autoimmune liver disease, cryptogenic cirrhosis, hemochromatosis, Wilson's disease, alpha-1-antitrypsin deficiency, and cholestatic liver diseases. STAT can be administered as an in vitro screening test to a patient having, or suspected of having, any chronic liver disease.

The non-invasive test methods disclosed herein are superior to each of these competitors in the abilities to detect early stage CLD and accurately monitor disease progression of, e.g., chronic hepatitis C, primary sclerosing cholangitis (PSC), nonalcoholic fatty liver disease (NAFLD), chronic hepatitis B, alcoholic liver disease, autoimmune liver disease, cryptogenic cirrhosis, hemochromatosis, Wilson's disease, alpha-1-antitrypsin deficiency, and cholestatic liver diseases. In a specific embodiment, the single-point STAT test is used as a screen to evaluate disease progression of chronic hepatitis C (CHC), primary sclerosing cholangitis (PSC) and Non-Alcoholic Fatty Liver Disease (NAFLD).

SUMMARY OF THE INVENTION

The disclosure provides a method for estimating portal blood flow and hepatic function in a subject comprising orally administering isotopically labeled cholic acid to a subject suspected of having or developing a hepatic disorder, for example, CHC, NAFLD or PSC. In one aspect, the STAT test is a simplified convenient test intended for screening purposes that can reasonably estimate the portal blood flow from a single blood sample taken 60 minutes after orally administered deuterated-cholate.

The previously disclosed Hepquant SHUNT test (SHUNT) involves oral and intravenous co-administration of distinguishable cholate compounds and collection and analysis of at least about 5 blood samples over intervals for about 90 minutes after administration. The SHUNT test gives cholate oral and intravenous clearances and liver shunt-comprehensive assessment of hepatic blood flow and hepatic function. The previously disclosed Hepquant FLOW test (FLOW) involves oral administration of a distinguishable cholate compound and collection and analysis of at least about 5 blood samples at intervals over about 90 minutes after administration to give oral cholate clearance (Portal circulation, portal hepatic filtration rate; Portal HFR). The herein disclosed Hepquant STAT test involves oral administration of a distinguishable cholate compound and collection of a single blood sample at a defined time point, for example, at 60 minutes after administration. It has been surprisingly discovered that analysis of a single blood sample can be used to estimate FLOW and also correlates with SHUNT. As liver disease progresses, FLOW, which assesses the portal blood flow, is reduced while SHUNT, which assesses portal-systemic shunting, is increased. STAT, which uses a single blood sample to infer the impaired FLOW, is also increased as liver disease progresses.

In one embodiment, the disclosure provides a method for estimation of portal blood flow in a subject, the method comprising: administering orally a distinguishable cholate compound to a subject with, or suspected of having or developing, a hepatic disorder, wherein no other distinguishable cholate is intravenously co-administered; collecting a blood sample from the subject at a single, specific time point after oral administration of the distinguishable cholate to the subject; measuring the concentration of the orally administered distinguishable cholate in the blood sample; and comparing the concentration of the distinguishable cholate in the blood sample to values or cutoffs of values established from a known patient population, as an estimation of portal blood flow in the subject.

In one aspect, the orally administered distinguishable cholate compound is an isotopically labeled cholic acid. In one aspect, the term cholic acid refers to the sodium salt of cholic acid. As used herein, the terms cholate compound, cholate and cholic acid are used interchangeably. In particular aspects, the isotopically labeled cholic acid is selected from 24-$^{13}$C cholic acid or 2,2,4,4-$^2$H cholic acid. In a specific aspect, the cholic acid is 2,2,4,4-$^2$H cholic acid. In various other aspects, the single blood sample is collected at one time point selected from about 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 minutes, or any time point in between, after oral administration of the distinguishable cholate compound. In a specific aspect, the blood sample is collected at any time point between 30 and 180 minutes. In particular aspects, the single blood sample is collected at one time point selected from about 45, 60 or 90 minutes after oral administration of the distinguishable cholate compound. In one specific aspect, the single blood sample is collected at about 60 minutes after oral administration of the distinguishable cholate compound. In another specific aspect, the single blood sample is collected at about 45 minutes after oral administration of the distinguishable cholate compound. In further aspects, the measuring step comprises quantifying the concentration of the distinguishable cholate compound in the sample by GC-MS or HPLC-MS. In a particular aspect, the sample is analyzed by HPLC-MS. In a specific aspect, the method further comprises the step of comparing the concentration of distinguishable cholate in the blood sample to the concentration of distinguishable cholate in one or more earlier samples from the same subject over time.

In another embodiment, when the concentration of the distinguishable cholate in the blood sample is above an established cutoff value in the comparing step of the STAT test, the method further comprises assessment of portal circulation by determining oral cholate clearance in the subject in the FLOW test; comprising the steps of administering orally an isotopically labeled cholic acid to a subject with, or suspected of having or developing, a hepatic disorder, wherein no additional cholic acid compound is intravenously co-administered; collecting samples from the subject over intervals for a period of less than 3 hours after administration of the agents to the subject; and measuring the clearance of the orally administered isotopically labeled cholic acid to assess portal circulation in the subject. In one aspect, the assessment of the portal circulation in the subject is an indicator of progression of at least one hepatic condition in a subject.

In a further embodiment, when the concentration of the distinguishable cholate in the blood sample is above an established cutoff value in the comparing step of the STAT test, the method further comprises assessment of cholate shunt in the subject; the additional SHUNT test comprising the steps of: administering orally a first distinguishable isotopically labeled cholic acid to a subject having, or suspected of having or developing, a hepatic disorder; co-administering intravenously a second distinguishable isotopically labeled cholic acid to the subject; collecting blood or serum samples over intervals for a period of less than 3 hours after administration of the agents to the subject; quantifying the first and the second isotopically labeled cholic acids in the samples by HPLC-MS; and calculating the cholic acid shunt using the formula: AUCoral/AUCiv× Doseiv/Doseoral×100%; wherein AUCoral is the area under the curve of the serum concentrations of the first cholic acid and AUCiv is the area under the curve of the second cholic acid; and wherein the cholate shunt is an indicator of hepatic function of the subject. In a preferred aspect, in the SHUNT test, the orally administering of the first labeled cholic acid and the intravenously co-administering of the second labeled cholic acid are performed simultaneously. In another preferred aspect, the additional SHUNT test the blood samples are collected from the subject at 5, 20, 45, 60 and 90 minutes post-dose.

In another embodiment, the disclosure provides for a kit of components for estimation of portal blood flow in a subject by the STAT test; the kit comprising a first component comprising one or more vials, each vial comprising a single oral dose of the distinguishable cholate compound; and a second component comprising one or more sets of labeled sterile blood-serum sample collection tubes. In one aspect, the kit further comprises one or more sets of labeled transport vials, each transport vial containing an internal cholic acid standard.

In another aspect, the kit also comprises a single box for both shipping the vials to a health care practitioner and shipping the samples from the health care practitioner to a reference lab for analysis. In another aspect, the kit includes the distinguishable cholate compound 2,2,4,4-$^2$H cholic acid. In various aspects, the $^2$H-cholic acid is in a powder form or in a solution form.

BRIEF DESCRIPTION OF THE DRAWINGS

FIG. 10A shows Portal HFR (FLOW) average test results in PSC patients compared to healthy controls.

FIG. 10B shows avg. MELD scores in 38 PSC patients.

FIG. 10C shows Portal HFR (FLOW) average test results in PSC patients not listed for transplant compared to PSC patients listed for liver transplant (LT).

FIG. 10D shows avg MELD scores in PSC patients not listed for transplant compared to PSC patients listed for LT.

FIG. 10E shows avg. Portal HFR (FLOW) test results in PSC patients without varices compared to PSC patients with varices.

FIG. 10F shows avg. MELD scores in PSC patients without varices compared to PSC patients with varices.

DETAILED DESCRIPTION OF THE INVENTION

Figure 1:
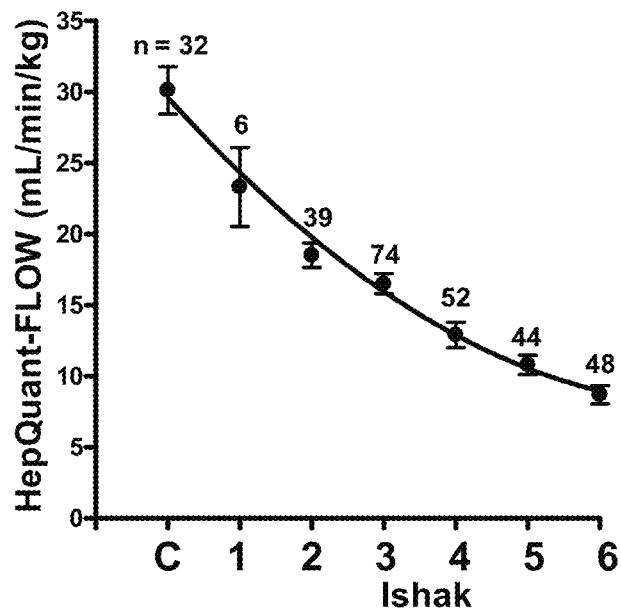
FIG. 1 shows results for the previously disclosed FLOW test in healthy controls and all stages of CHC. Data from HALT-C (later stage CHC, stably compensated, Ishak F2-6) was combined with data from the Early CHC Study (healthy controls (C) and early stage CHC, Ishak F1-2) and a study of healthy donors for living donor liver transplantation (healthy controls (C)). The F2 patient data was not different between studies and was combined. The portal blood flow (mean+/−SEM) for healthy controls and patients with all stages of CHC was graphed as a continuous function demonstrating the ability to assess the entire spectrum of disease. The n for each group is indicated above its symbol. HepQuant FLOW testing could increase early detection of liver disease when it is most treatable.

The methods and tests disclosed herein are based on a new view of chronic liver disease, that it is the disruption of the portal blood flow, not fibrosis per se, that is deleterious and should be targeted for analysis of liver function.

One example of chronic liver disease is NAFLD which can progress from simple fatty liver called steatosis, which is relatively benign, to the more serious Non-Alcoholic SteatoHepatitis (NASH). Hepatitis can be also be caused by excessive drinking as in Alcoholic SteatoHepatitis (ASH), or viral infection, i.e. Chronic Hepatitis C (CHC). Another chronic liver disease is PSC. All these chronic liver diseases (CLDs) are characterized by a similar patho-physiology with inflammation, cell death, and fibrosis leading to a progressive disruption of the hepatic microvasculature so a test to measure portal blood flow will work for assessment of all CLD.

Almost all the other proposed tests to assess chronic liver disease have focused on fibrosis, either on serum biomarkers or the change in tissue elasticity (Mukherjee and Sorrell, 2006, Noninvasive tests for liver fibrosis. Semin Liver Dis. 26: 337-347; Manning and Afdhal, 2008. Diagnosis and quantitation of fibrosis. Gastroenterology. 134: 1670-1681; Poynard et al., 2008, Concordance in a world without a gold standard: A new non-invasive methodology for improving accuracy of fibrosis markers. PLoS One. 3: e3857).

Both fibrosis and microvasculature disruption do increase as disease progresses but they are not perfectly linked. This explains why patients with extreme fibrosis, cirrhosis, can remain stable as long as their portal flow is maintained above a critical threshold. It also explains why those patients with only moderate fibrosis but severely impaired flow can have serious complications. This new insight can change the whole focus of liver disease assessment. By targeting the portal flow physicians can easily detect early stage liver disease, accurately assess the status of their patients, and predict clinical outcomes. More effective treatments for liver disease can result from having research on new therapies and new drugs focus on improving and/or maintaining the portal flow.

The new focus on portal flow could revolutionize how chronic liver disease is staged and monitored. Biopsy would still be useful in the initial diagnosis to rule out auto-immune disease and inherited disorders but would not be used to assess patients' status or follow them over time. Impairment of portal flow would be used to guide management and determine when it would be appropriate to screen for varices and hepatocellular carcinoma. Portal flow would be a new more accurately determined endpoint for clinical trials.

In one embodiment, the STAT test is utilized to estimate portal blood flow and screen large populations for detection of patients with chronic liver disease, including chronic hepatitis C, PSC and NAFLD. The herein disclosed STAT test is intended for screening purposes. The relationship of STAT to prior art methods of determining clearance of cholate from the portal circulation, specifically the FLOW and SHUNT tests, has been validated using a large cohort of patients with chronic hepatitis C. The use of FLOW and SHUNT tests with respect to patients with chronic hepatitis C was the subject of prior applications US 2010/0055734 and US2008/0279766, which are each incorporated herein by reference. In various aspects, STAT is used for defining disease severity in patients with chronic hepatitis C, tracking disease progression and response to treatments.

Highly conserved enteric transporters (ISBT, MRP3) specifically target oral cholate to the portal circulation. Highly conserved hepatic transporters (NTCP, OATPs) clear cholate from the portal and systemic circulation. Therefore, noninvasive quantitative assessment of the portal circulation can be performed by administration to a patient of a distinguishable cholate compound and assessment of a level of the distinguishable cholate compound in blood samples drawn at various multiple time points to determine an oral clearance curve.

The oral cholate clearance (dose/area under oral clearance curve) is a measure of the effective portal blood flow (FLOW). The IV cholate clearance (dose/area under IV clearance curve) is a measure of the total hepatic blood flow. The ratio of IV to oral clearances assesses the portal-systemic shunt fraction (SHUNT). In one aspect, the disclosure provides methods wherein the oral cholate clearance can be estimated from the oral cholate serum concentration at a single time point, for example, at 60 minutes after administration (STAT).

In the diseased liver, as more blood escapes extraction by intra- and extra-hepatic shunting to the systemic circulation, the SHUNT increases, HFR or portal flow decreases, and STAT increases. In a normal control subject, the effective portal blood flow (FLOW) is high in a healthy liver due to low vascular resistance. Portal-systemic shunting (SHUNT) is minimal. Oral cholate at 60 min (STAT) is low. For example, in a healthy control FLOW=37 mL min$^{-1}$ kg$^{-1}$, SHUNT=18% and STAT=0.2 µM. However, in a subject with liver disease, inflammation, fibrosis, and increased vascular resistance reduce the effective portal blood flow (FLOW). Portal-systemic shunting (SHUNT) is increased. Oral cholate at 60 min (STAT) is high. For example in a CHC F2 patient, FLOW=9 mL min$^{-1}$ kg$^{-1}$, SHUNT=35% and STAT=1.6 µM.

In another embodiment, STAT can be utilized for estimating portal blood flow and use as a screening test in detecting, defining disease severity, tracking disease progression and monitoring response to treatment in patients having, or suspected of having, Non-Alcoholic Fatty Liver Disease (NAFLD). In one aspect, the STAT test can be used a screening test to aid the physician in distinguishing NASH from steatosis, as well as a screening test in detecting, defining disease severity, tracking disease progression and monitoring response to treatment in patients having NASH.

In other embodiments, STAT is applicable for estimating portal blood flow and use as a screening test in any chronic liver disease. For example, in various aspects, STAT can be used as a screening test in detecting, defining disease severity, tracking disease progression and monitoring response to treatment in patients having, or suspected of having, any chronic liver disease, such as, but not limited to, chronic hepatitis C, nonalcoholic fatty liver disease (NAFLD), chronic hepatitis B, alcoholic liver disease, non-alcoholic steatohepatitis (NASH), autoimmune liver disease, cryptogenic cirrhosis, hemochromatosis, Wilson's disease, alpha-1-antitrypsin deficiency, and cholestatic liver diseases.

Orally Administered Compound

In various embodiments, portal flow can be assessed utilizing any orally administered test compound with the following characteristics: 100% absorption following oral administration, high hepatic extraction (>70% in first pass through the liver of a healthy subject), and removal from the blood or plasma exclusively by the liver. The test compound for measurement of portal flow can be an endogenous compound or a xenobiotic.

Several endogenous bile acids and bile acid conjugates meet these criteria; for example, the test compound can be selected from cholic acid, any glycine conjugate of cholic acid, any taurine conjugate of cholic acid; chenodeoxycholic acid, any glycine conjugate of chenodeoxycholic acid, any taurine conjugate of chenodeoxycholic acid; deoxycholic acid, any glycine conjugate of deoxycholic acid, any taurine conjugate of deoxycholic acid; or lithocholic acid, or any glycine conjugate or taurine conjugate thereof. In various aspects, any bile acid or bile acid conjugate may be in the form of a physiologically acceptable salt, e.g., the sodium salt of cholic acid. In one aspect, the term cholic acid refers to the sodium salt of cholic acid. Cholic acid (cholate) is the test compound in a preferred embodiment. As used herein, the terms cholate compound, cholate and cholic acid are used interchangeably.

Xenobiotics that could be administered orally and also have high first pass hepatic elimination could include, but are not limited to, propanolol, nitroglycerin or derivative of nitroglycerin, or galactose and related compounds.

In one aspect, the test compound is propranolol. Propranolol is a nonselective blocker and has been shown to be effective for the prevention of variceal bleeding and rebleeding and is widely used as the pharmacotherapy for the treatment of portal hypertension in patients with cirrhosis. (Suk et al. 2007, Effect of propranolol on portal pressure and systemic hemodynamics in patients with liver cirrhosis and portal hypertension: a prospective study. Gut and Liver 1 (2): 159-164). Propranolol is almost entirely cleared by the liver. It has been demonstrated that total (+)-propranolol plasma clearance constitutes a good estimate of hepatic blood flow in patients with normal liver function. (Weiss et al., 1978 (+)-Propranolol clearance, an estimation of hepatic blood flow in man, Br. J. Clin. Pharmacol. 5: 457-460).

In another aspect, the test compound is isosorbide 5-mononitrate. This compound can be administered orally and detected in plasma by HPLC-EIMS. (Sun et al., High performance liquid chromatography-electrospray ionization mass spectrometric determination of isosorbide 5-mononitrate in human plasma, J. Chromatogr. B Analyt. Technol. Biomed. Sci. 2007 Feb. 1; 846(1-2):323-8).

In one aspect, the test compound is galactose. Galactose elimination capacity (GEC) has been used as an index of residual hepatic function. Galactose in the GEC test typically is administered intravenously at a dose of 0.5 mg/kg and venous samples taken every 5 min between 20 and 60 minutes. The clearance of galactose is decreased in individuals with chronic liver disease and cirrhosis. The fact that this carbohydrate has a high extraction ratio, however, makes the metabolism of galactose dependent on liver blood flow and hepatic functional mass. (Tygstrup N, Determination of the hepatic elimination capacity (Lm) of galactose by a single injection, Scand J Lab Clin invest, 18 Suppl 92, 1966, 118-126). The carbohydrate galactose is metabolized almost exclusively in the liver, and the elimination rate at blood concentrations high enough to yield near-saturated enzymatic conversion, the GEC is used as a quantitative measure of the metabolic capacity of the liver. One study has shown that among patients with a newly-diagnosed cirrhosis and a decreased GEC, the GEC was a strong predictor of mortality. (Jepsen et al, 2009, The galactose elimination capacity and mortality in 781 Danish patients with newly-diagnosed liver cirrhosis: a cohort study. BMC Gastroenterol. 2009, 9:50).

In certain aspects, one or more differentiable isotopes is incorporated into the selected test compound in order to be utilized to assess hepatic function. The differentiable isotope can be either a radioactive or a stable isotope incorporated into the test compound. Stable ($^{13}C$, $^{2}H$, $^{15}N$, $^{18}O$) or radioactive isotopes ($^{14}C$, $^{3}H$, Tc-99m) can be used. Advantages of stable isotopes are the lack of exposure to radioactivity, natural abundance, and the specificity of the analyses used for test compound identification (mass determination by mass spectrometry). Stable isotopically labeled compounds are commercially available. For example, $^{13}C$- and $^{2}H$-labeled cholic acid compounds can be purchased from Sigma-Aldrich, CDN Isotopes and Cambridge Isotope Laboratories, Inc.

In other aspects, the test compound may be an unlabeled endogenous compound, such as unlabeled cholate. In the aspect using an unlabeled endogenous compound, the oral test dose is sufficiently great, for example 2.5-7.5 mg/kg cholate, for the resulting serum concentration to be distinguishable above the baseline serum concentration of that endogenous compound.

The platform for detecting and measuring the test compound in the blood sample from the subject is dependent on the type of administered test compound. For stable isotopes, the concentration of the test compound in a blood sample can be measured by, e.g. GC/MS or LC/MS. For radiolabeled test compounds, e.g., scintillation spectroscopy can be employed. For analysis of unlabeled compounds, e.g., autoanalyzers, luminescence, or ELISA can be employed. It is further contemplated that strip tests with a color developer sensitive directly or indirectly to the presence and quantity of test compound can be employed for use in a home test or a point of care test.

Portal Blood Flow

The portal blood flow can be non-invasively and accurately quantified by exploiting the unique physiology of the endogenous bile acid, cholate, which can be labeled, for example, with safe non-radioactive stable isotopes. One such liver function test, called the FLOW test, accurately measures the portal blood flow from a minimum of 5 blood samples taken over a period of 90 minutes after an oral dose of deuterated-cholate. The FLOW test is disclosed in Everson, US 2010/0055734, Methods for Diagnosis and Intervention of Hepatic Disorders, filed Sep. 11, 2009, which is incorporated herein by reference. If an additional simultaneous IV dose of $^{13}C$-cholate is administered concurrently with the oral dose of deuterated-cholate, then the SHUNT test can also measure the systemic hepatic blood flow and thus the amount of portal-systemic shunting. The SHUNT test is disclosed in Everson et al., US2008/0279766, Methods for Diagnosis and Intervention of Hepatic Disorders, filed Jan. 26, 2006, which is incorporated herein by reference. The present disclosure provides a simplified test method called the STAT test which is a simplified convenient test intended for screening purposes that can reasonably estimate the portal blood flow from a single blood sample taken at a single time point, e.g., 60 minutes after oral administration of a distinguishable cholate compound, e.g., a deuterated cholate. A comparison of typical embodiments of SHUNT, FLOW and the herein disclosed STAT tests is shown in Table 1 below.

TABLE 1

| Liver Function Tests. | | | | |
| --- | --- | --- | --- | --- |
| Test Name | Test Compound | Route of Administration | Samples | What is Measured or Defined |
| SHUNT | $^{13}C$-cholate 4D-$^{2}H$-cholate | Intravenous Oral | n = 5 over 90 min | Clearances and Shunt-comprehensive assessment of hepatic blood flow and hepatic function |

TABLE 1-continued

Liver Function Tests.

| Test Name | Test Compound | Route of Administration | Samples | What is Measured or Defined |
|---|---|---|---|---|
| FLOW | 4D-$^2$H-cholate | Oral | n = 5 over 90 min | Portal circulation (portal hepatic filtration rate; Portal HFR) |
| STAT | 4D-$^2$H-cholate | Oral | n = 1 at 60 min | Estimates FLOW and correlates with SHUNT |

Figure 2:
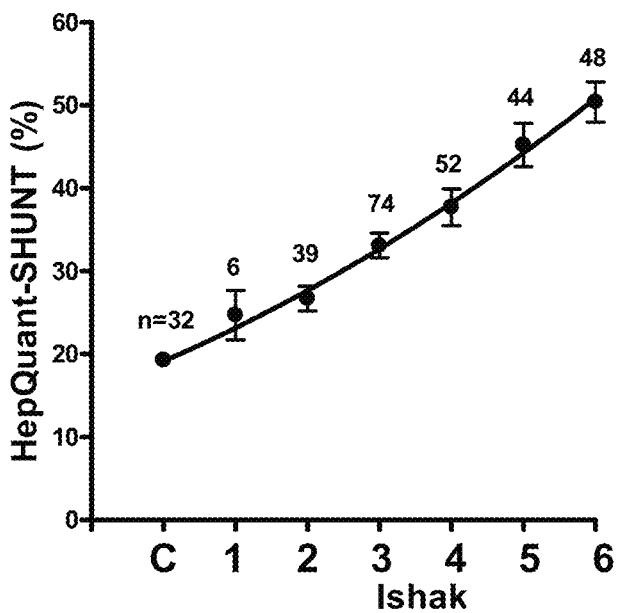
FIG. 2 shows data for the previously disclosed SHUNT test in Healthy Controls and All Stages of CHC. Data from HALT-C was combined with data from the Early CHC Study (healthy controls (C) and early stage CHC, Ishak F1-2) and a study of healthy donors for living donor liver transplantation (healthy controls (C)). The F2 patient data was not different between studies and was combined. The portal-systemic shunt fraction (mean+/−SEM) for healthy controls and patients with all stages of CHC was graphed as a continuous function demonstrating the ability to assess the entire spectrum of disease. The n for each group is indicated above its symbol. Increased variability at F1 is due to the small number of patients that were diagnosed at this early stage. HepQuant SHUNT testing could increase early detection of liver disease when it is most treatable.
Figure 3:
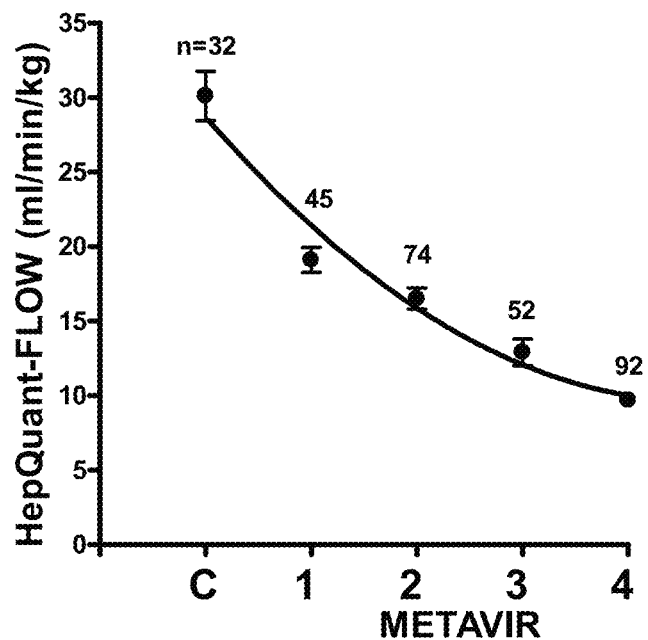
FIG. 3 shows data for the previously disclosed FLOW test in Healthy Controls and All Stages of CHC. Data from HALT-C (later stage CHC, stably compensated, METAVIR F1-4) was combined with data from the Early CHC Study (healthy controls (C) and early stage CHC, METAVIR F1) and a study of healthy donors for living donor liver transplantation (healthy controls (C)). The F1 patient data was not different between studies and was combined. The portal blood flow (mean+/−SEM) for healthy controls and patients with all stages of CHC was graphed as a continuous function demonstrating the ability to assess the entire spectrum of disease. The n for each group is indicated above its symbol.
Figure 4:
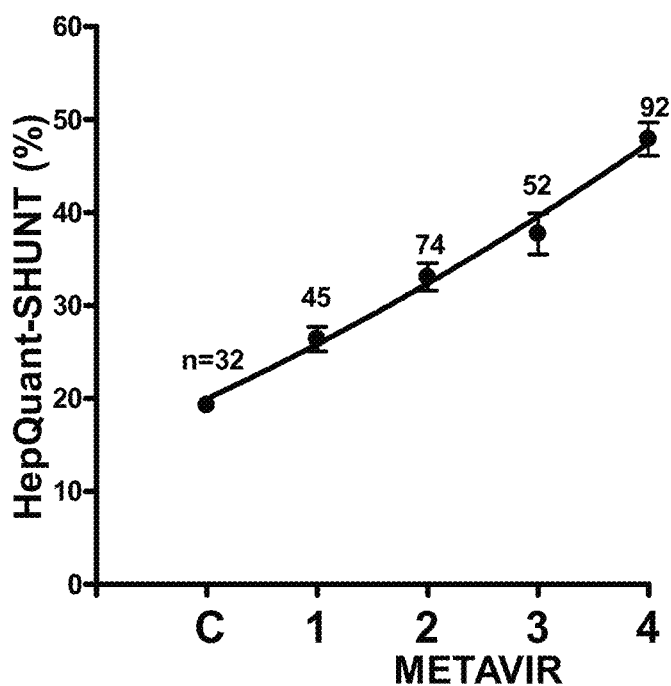
FIG. 4 shows data for the previously disclosed SHUNT test in Healthy Controls and All Stages of CHC. Data from HALT-C (later stage CHC, stably compensated, METAVIR F1-4) was combined with data from the Early CHC Study (healthy controls (C) and early stage CHC, METAVIR F1) and a study of healthy donors for living donor liver transplantation (healthy controls (C)). The F1 patient data was not different between studies and was combined. The portal-systemic shunt fraction (mean+/−SEM) for healthy controls and patients with all stages of CHC was graphed as a continuous function demonstrating the ability to assess the entire spectrum of disease. The n for each group is indicated above its symbol.

Research versions of the FLOW and SHUNT tests were compared to other proposed liver tests in the HALT-C trial of Chronic Hepatitis C (CHC) patients with moderate to advanced fibrosis (Ishak F2-6) and in the Early CHC study of healthy controls and early stage (Ishak F1-2) patients. FLOW and SHUNT correlated with fibrosis stage, prevalence of cirrhosis, prevalence of varices, and variceal size (Everson et al. 2008, The spectrum of hepatic functional impairment in compensated chronic Hepatitis C: Results from the Hepatitis C anti-viral long-term treatment against cirrhosis trial. Aliment Pharmacol Ther. 27: 798-809; Everson et al., 2007. Portal-systemic shunting in patients with fibrosis or cirrhosis due to chronic hepatitis c: The minimal model for measuring cholate clearances and shunt. Aliment Pharmacol Ther. 26: 401-410) and could track improvement after SVR (Everson et al., 2009. Quantitative tests of liver function measure hepatic improvement after sustained virological response: Results from the HALT-C trial. Aliment Pharmacol Ther. 29: 589-601). FLOW was superior to all other tests and even biopsy in predicting clinical outcomes (Everson, et al, submitted to Gastroenterology). FLOW and SHUNT were the only tests that could detect hepatic dysfunction in early CHC patients compared to healthy controls (Helmke, et al., submitted to Alimentary Pharmacology and Therapeutics). FLOW data (portal blood flow) from controls (C) and patients from both studies was combined and graphed (mean+/−SEM, the n for each group indicated above its symbol) as a continuous function demonstrating the ability to assess the entire spectrum of disease and compared to the Ishak score, see FIG. 1. In a similar manner, SHUNT continuously increased with disease progression (Everson et al. 2008, infra) as shown in FIG. 2. I HepQuant FLOW, SHUNT and STAT testing can be used to assess the entire spectrum of NAFLD.

Surprisingly, it has been discovered in a major study of almost 300 CHC patients, portal flow measured by cholate testing was superior in predicting clinical outcomes to the current gold standard of fibrosis measured by biopsy (Everson et al, 2011). In the Early CHC study impairment of the portal flow and increased shunting measured by cholate testing was the earliest detectable pathophysiology. These results have lead to a new understanding of CLD that it is the disruption of hepatic microvasculature and not fibrosis per se that is deleterious. This microvasculature disruption impairs the portal blood flow which can be non-invasively and accurately quantified by exploiting the unique physiology of the endogenous bile acid, cholate.

Portal blood flow has been found to be the key to liver assessment. The liver receives ~75% of its blood through the portal vein which brings in the nutrients for processing and deleterious compounds for detoxification. This low blood pressure system is sensitive to the earliest disruption of the microvasculature so that the early stages of CLD can be detected by decreased portal flow and increased shunting before any other physiological impacts. The high pressure hepatic systemic blood flow is decreased less and only later in the disease process. Unlike biopsy which samples only 1/50,000$^{th}$ of the liver, the portal flow is a measure of the entire organ. As disease progresses there is increasing disruption of the microvasculature architecture and increasing impairment of portal flow which causes the major manifestations of advanced CLD. Impaired flow causes ascites, portal hypertension, and esophageal varices. Impaired flow causes increased shunting of toxins which leads to hepatic encephalopathy.

Cholate is a unique probe of the portal blood flow and the hepatic systemic flow. Many liver tests have attempted to use the clearance of oral or IV compounds but only cholate has succeeded in assessing early and late stage CLD. Other oral compounds are absorbed at various sites along the GI tract and do not target the portal circulation. Other compounds are taken up by nonspecific transporters. Oral cholate is specifically absorbed by the terminal ileum epithelial cells via the high affinity ileal Na$^+$-dependent bile salt transporter (ISBT) and is effluxed by MRP3 transporters directly into the portal blood flow (Trauner and Boyer, 2003, Bile salt transporters: Molecular characterization, function, and regulation. Physiol Rev. 83: 633-671). A different set of high affinity transporters including the Na$^+$/taurocholate cotransporter (NTCP) and organic anion transporting proteins (OATPs) then takes it up into hepatocytes with highly efficient first pass extraction (Trauner and Boyer, 2003, infra) so that any cholate that escapes extraction is a direct measure of the portal flow. Once intracellular, it is rapidly conjugated to glycine and taurine so that the unconjugated form does not then re-appear in the intrahepatic circulation, which would confuse the pharmacokinetics. Other unconjugated bile salts such as deoxycholate and chenodeoxycholate would behave similarly but they are much stronger solubilizing agents and would not be as safe to administer. Patient safety is ensured by using a stable isotope labeled endogenous compound avoiding the risks of xenobiotic or radiation exposure. All the proteins and systems involved are highly conserved and essential so that the pharmacokinetics of cholate are consistent between individuals and not affected by gender, age, or genetic makeup, or by diet or concomitant medications.

Previously, human studies demonstrated the clinical utility of FLOW and SHUNT testing in CHC. A number of new liver tests have been proposed over the years but there have been few studies to directly compare their efficacy and actual clinical utility. A very large multicenter HALT-C trial was conducted whose main objective was to determine the efficacy of long term hepatitis C virus suppression but which also included an ancillary study to evaluate a battery of new quantitative liver function tests. (Everson et al., 2009. Quantitative tests of liver function measure hepatic improvement after sustained virological response: Results from the HALT-C trial. Aliment Pharmacol Ther. 29: 589-601). Nearly 300 patients with advanced (Ishak F2-6) but compensated CLD were tested. A recently completed Early CHC study compared these tests in 25 healthy controls and 23 early stage (Ishak F1-2) CHC patients in order to examine the entire spectrum of this CLD. The liver's metabolic capacity was assessed using caffeine, antipyrine, lidocaine, and galactose tests. All these activities were reduced in patients with cirrhosis, but none were different in early stage CHC patients compared to healthy controls. (Everson et al., 2008. The spectrum of hepatic functional impairment in compensated chronic hepatitis c: Results from the hepatitis c anti-viral long-term treatment against cirrhosis trial. Aliment Pharmacol Ther. 27: 798-809). These results suggest that metabolic capacity is maintained until there is significant loss of functional parenchyma in later stage CLD. In HALT-C the patients were tested serially every 2 years and followed to monitor outcomes. FLOW, using a cutoff of <9.5 ml/min/kg, was superior to the other tests in predicting clinical outcomes with the highest sensitivity, specificity, positive predictive value, negative predictive value and the best performance by ROC analysis (Quantitative Liver Function Tests Improve the Prediction of Clinical Outcomes in Chronic Hepatitis C: Results from the HALT-C Trial, Everson et al, submitted to Gastroenterology). FLOW had a higher ROC c statistic (0.84) relative to SHUNT (0.79). The improvement after SVR was more significant for FLOW ($p=0.0002$) than for SHUNT ($p=0.0003$) (Everson et al., 2009, infra). In the Early CHC study, FLOW decreased from $34\pm14$ ml/min/kg (mean±SD) in controls to $23\pm10$ ml/min/kg in early CHC ($p<0.002$) but the increase in SHUNT ($20\pm6\%$ in controls vs, $31\pm14\%$ in early CHC patients $p<0.0002$) was more statistically significant. None of the other tests could distinguish early stage CHC patients from healthy controls. These results suggest that SHUNT and FLOW outperform other functional tests in detecting early liver disease, tracking patients, and predicting clinical outcomes.

In order to transform the research tests into viable commercial clinical tests, a number of advances were made to increase patient convenience, simplify analysis, and increase accuracy. In the published studies, 14 blood samples were taken over 180 minutes after administration of labeled cholates to define the clearance curves. The pharmacokinetics of these curves are remarkably consistent due to the conservation of the underlying systems. Over 500 HALT-C studies were analyzed to demonstrate that only 5 blood samples obtained at 5, 20, 45, 60, and 90 minutes could mathematically model these curves with 98% accuracy of the 14 point method (Everson et al., 2007. Portal-systemic shunting in patients with fibrosis or cirrhosis due to chronic hepatitis c: The minimal model for measuring cholate clearances and shunt. Aliment Pharmacol Ther. 26: 401-410). This greatly reduces patient blood requirements and time commitment and laboratory sample processing efforts. Previously a complicated gas chromatography-mass spectrometry (GCMS) method required days for complex chemical derivatizations and long analytical runs. A robust LCMS method was developed, eliminating chemical derivatization required in the GCMS method, and reducing sample processing from days to 3 hours while increasing recovery, reproducibility, and accuracy. The LCMS technique has been validated according to FDA guidelines for selectivity, accuracy, precision, recovery, stability, and freedom from interferences by serum components or concomitant medications.

The STAT test is different from the SHUNT and FLOW tests in that only a single blood sample is drawn from the patient making the test more economical in terms of requiring less clinical personnel time, instrumentation time, and fewer clinical and laboratory supplies. For example, a single blood draw does not require an indwelling catheter. Preparation of a single sample is also less prone to error than multiple sequential samples. The test is also more comfortable for the patient and requires less time spent at the clinic Rationale and Study Design for the Application of HepQuant Testing to NAFLD There is an expected similarity in disease progression of NAFLD and CHC. In one aspect of the disclosure, it is feasible to assess the entire spectrum of NAFLD because the pathophysiological progression is very similar to that of CHC. Progression is typically described by 4 stages of histologically described fibrosis. In both the CHC Metavir system (Group, TFMCS. 1994. Intraobserver and interobserver variations in liver biopsy interpretation in patients with chronic hepatitis C Hepatology. 20: 15-20) and NASH system (Brunt et al., 1999, Nonalcoholic steatohepatitis: A proposal for grading and staging the histological lesions. Am J Gastroenterol. 94: 2467-2474; Kleiner et al., 2005. Design and validation of a histological scoring system for nonalcoholic fatty liver disease. Hepatology. 41: 1313-1321) the absence of observable fibrosis is scored F0. Early stage fibrosis, F1, tends to be more periportal in CHC and can be periportal and/or perisinusoidal in NASH. In both scoring systems, F2 is more extensive periportal and perisinusoidal fibrosis, F3 is bridging fibrosis, and F4 is cirrhosis (Group, TFMCS. 1994; Brunt et al., 1999; Kleiner et al., 2005; Goodman, Z D. 2007. Grading and staging systems for inflammation and fibrosis in chronic liver diseases. J Hepatol. 47: 598-607). Because of this similar pattern of progression, it is expected that the portal flow impairment in NASH patients at stages F1-F4 to be comparable to CHC patients at corresponding Metavir stages F1-F4. Our previous CHC data stratified according to the 6 stage Ishak system can be readily converted (Goodman et al., 2007, infra) to the Metavir system to allow the estimation described below of the expected effect size, the number of subjects required, and approximate power of our proposed study. The correlation between scoring systems for FLOW and Ishak scoring, SHUNT and Ishak scoring, FLOW and Metavir scoring, and SHUNT and Metavir scoring is shown in FIGS. 1-4, respectively.

Impact of Liver Testing in the Early Stages of Chronic Liver Disease. While most previous test development has focused on detecting advanced fibrosis and cirrhosis, it has been argued that the most serious need in NAFLD is the ability to distinguish early stage NASH from simple steatosis (Wilson and Chalasani, N. 2007. Noninvasive markers of advanced histology in nonalcoholic fatty liver disease: Are we there yet? Gastroenterology. 133: 1377-1378; discussion 1378-1379; and Vuppalanchi and Chalasani 2009. Nonalcoholic fatty liver disease and nonalcoholic steatohepatitis: Selected practical issues in their evaluation and management. Hepatology. 49: 306-317). The FLOW and SHUNT tests could detect the hepatic dysfunction of NASH patents and differentiate them from those with simple steatosis which are expected to have near normal portal flow.

In contrast to the FLOW and SHUNT tests, which require a minimum of 5 blood samples drawn from the patient over a period of 90 minutes or more following distinguishably-labeled cholate administration, it has been surprisingly discovered that results from a test including a single blood sample drawn after oral administration of a distinguishably-labeled cholate compound correlate to the results from both the FLOW and SHUNT tests. The single time point screening test is called the STAT test.

The time point for the STAT test single blood draw from the patient can be selected from, for example, any time point following oral administration of a distinguishable cholate; for example any time point selected from between about 10 and about 180 minutes post-administration. In one aspect, the time point is a single time point selected between about 20 and about 120 minutes post-administration. In another aspect, the time point is a single time point selected between about 30 and about 90 minutes post-administration. In one aspect the blood sample is drawn from the patient at any time point selected from about 30, 35, 40, 45, 50, 55, 60, 65, 70, 75, 80, 85, or 90 minutes, or any time point in between, post oral administration of the distinguishable cholate. In one aspect the time point for the single blood draw is selected from one of about 45, about 60 or about 90 minutes post administration. In one particular aspect, the single blood sample is drawn from the patient at about 45 minutes post administration. See for example, FIG. 5, where the results of the STAT test at 45 minutes post administration, are compared to the FLOW test. In another particular aspect, the single blood sample is drawn from the patient at about 60 minutes post oral administration of a distinguishable cholate. See for example, FIG. 8, where the results of the STAT test at 60 minutes post administration, are compared to the FLOW test. The cholate concentrations at 60 minutes have been converted by the equation into estimated flow rates (mL/min/kg) and compared to the actual FLOW test results.

In one embodiment, the distinguishable cholate for oral administration can be any distinguishable cholate compound that is distinguishable analytically from an endogenous cholic acid. In one aspect, the distinguishable cholate compound is selected from any isotopically labeled cholic acid compound known in the art. Distinguishable cholate compounds used in any one of these assays might be labeled with either stable ($^{13}C$, $^{2}H$, $^{18}O$) or radioactive ($^{14}C$, $^{3}H$) isotopes. Distinguishable cholate compounds can be purchased (for example CDN Isotopes Inc., Quebec, CA). In a preferred aspect, the distinguishable cholate is selected from any known safe, non-radioactive stable isotope of cholic acid. In one specific aspect, the distinguishable cholate compound is 2,2,4,4-$^{2}H$ cholic acid. In another specific aspect, the distinguishable cholate compound is 24-$^{13}C$ cholic acid.

In one aspect, STAT is used as a screening test for a patient having or suspected of having PSC. A STAT test result of 0.4±0.1 indicates a healthy patient. In patients diagnosed with PSC, 0.7±0.5 indicates PSC without PHTN, 1.6±1.5 indicates PSC with PHTN (splenomegaly or varices), 2.2±1.4 indicates PSC with varices, and 3.7±0.9 indicates PSC decompensated (varceal bleed or ascites). In another aspect, a STAT result indicates the patient should be followed with additional tests, such as FLOW, SHUNT or other diagnostic tests. See, e.g., FIGS. 6 and 7.

In one aspect, the STAT test is used as a screening test for a patient having or suspected of having NAFLD. Hepatitis can also be caused by excessive drinking as in Alcoholic SteatoHepatitis (ASH), or viral infection, i.e. Chronic Hepatitis C (CHC). All these chronic liver diseases (CLDs) are characterized by a similar patho-physiology with inflammation, cell death, and fibrosis leading to a progressive disruption of the hepatic microvasculature so, in various aspects, the STAT test will work on all CLD.

In another aspect, the single-point STAT test is used as an in vitro screen for disease progression of any chronic liver disease. For example, an individual patient diagnosed with, e.g., chronic hepatitis C, chronic hepatitis B, cytomegalovirus, Epstein Barr virus, alcoholic liver disease, amiodarone toxicity, methotrexate toxicity, nitrofurantoin toxicity, NAFLD, PSC, haemochromatosis, Wilson's disease, autoimmune chronic hepatitis, primary biliary cirrhosis, primary sclerosing cholangitis, or hepatocellular carcinoma, may be monitored over time using the STAT test.

In another aspect, the STAT test result is an indication of portal blood flow in any patient. The STAT test is being developed especially to screen large numbers of potential patients. Those with a suspiciously low estimated portal flow would be referred for a FLOW or SHUNT test to more precisely assess hepatic impairment in early stage NASH. Patients with NASH need to be regularly monitored for progression in order to predict the course of their disease (Soderberg et al., 2010, Decreased survival of subjects with elevated liver function tests during a 28-year follow-up. Hepatology. 51: 595-602; Rafiq et al., 2009, Long-term follow-up of patients with nonalcoholic fatty liver. Clin Gastroenterol Hepatol. 7: 234-238). The prognostic utility of biopsy in NAFLD has been questioned (Angulo, P. 2010. Long-term mortality in nonalcoholic fatty liver disease: Is liver histology of any prognostic significance? Hepatology. 51: 373-375). FLOW and SHUNT testing was found to be superior to biopsy in predicting outcomes in CHC and is expected to be superior in NAFLD as well.

In another aspect, the STAT test is used to monitor effectiveness of treatment for a patient with liver disease. In one aspect the treatment is antiviral treatment.

In another aspect, the STAT test is used to prioritize patients waiting for a liver transplant. In one aspect, the patients waiting for liver transplant are patients with PSC, NASH, or chronic HCV.

In one embodiment, the STAT test is a non-invasive, in vitro test used to screen patients for liver function or liver disease; monitor liver disease patients undergoing antiviral therapy; monitor disease progression in patients with chronic liver disease; determine stage of disease in a patient diagnosed with HCV or PSC; prioritize liver disease patients for liver transplant; determine selection of patients with chronic hepatitis B who should receive antiviral therapy; assessing the risk of hepatic decompensation in patients with hepatocellular carcinoma (HCC) being evaluated for hepatic resection; identifying a subgroup of patients on waiting list with low MELD (Model for End-stage Liver Disease score) who are at-risk for dying while waiting for an organ donor; as an endpoint in clinical trials; replacing liver biopsy in pediatric populations; tracking of allograft function; measuring return of function in living donors; measuring functional impairment in cholestatic liver disease (PSC, Primary Sclerosing Cholangitis); or, used in combination with ALT to identify early stage F0-F2 HCV patients.

Kits

In still further embodiments, the disclosure provides kits for use with the methods and comparison methods described herein. The distinguishable cholate provided in a kit is employed in an in vitro test to assess liver health in a health facility and/or a home kit format. Results of the test can be used in accordance with FIG. 7. For Example, a patient suspected of having a disease or condition can be tested with the STAT test after undergoing a History or Physical Exam or standard lab tests. A low test result ("A" range) will suggest the patient be followed with a yearly exam. An intermediate result ("B" range) will indicate the patient should be tested with either the FLOW or SHUNT test. A high result ("C" range) indicates the patient should be suspected of having an advanced stage of disease and should, e.g. undergo esophagogastroduodenoscopy (EGD) or hepatocellular carcinoma (HCC) screening.

Distinguishable cholate compound is used as a hepatic blood flow assessing agent and may comprise, a suitable container means, an oral dose of distinguishable cholate to possibly be administered in an outpatient facility, within a hospital setting, or outside of a hospital environment. Sample tubes for collection of the blood samples are also included. In one example, a kit may comprise an oral dose of the distinguishable cholate and sample tubes for collection of a single sample following a period of, for example, selected from a specific time point from about 10 to about 200 minutes after oral administration of the distinguishable cholate. In a specific example, one blood sample is collected at a time point of about 45 minutes after administration of the distinguishable cholate. In another specific example one blood sample is collected at a time period of about 60 minutes after administration of the distinguishable cholate. In a further example, a kit may comprise components necessary for a test period of 30 minutes post administration of distinguishable agents. The kits may further comprise a suitably aliquoted composition of the specific agent such as cholate, or a diagnostic pharmaceutical composition comprising a distinguishable cholate, whether labeled or unlabeled, as may be used to prepare a standard curve for a detection assay. The diagnostic pharmaceutical composition comprising a distinguishable cholate may contain additional pharmaceutically acceptable excipients and/or vehicles as known in the art.

The container means of the kits will generally include at least one vial, test tube, flask, bottle, syringe or other container means, into which the distinguishable agent may be placed, and preferably, suitably aliquoted. The kits of the present invention will also typically include a means for containing the distinguishable agent and any other reagent containers in close confinement for commercial sale. Such containers may include injection or blow-molded plastic containers into which the desired vials are retained. In addition, the kits may contain a product for diluting the distinguishable oral agent.

In embodiments, the kit may further include instructions for comparing the amount of distinguishable cholate compound to a cutoff value or cutoffs of values to determine the state of portal blood flow and/or hepatic function in the patient.

Preparation of Quality Control Samples for Kits

The FDA provides guidance as to acceptable levels of accuracy and precision of analytical methods. See, for example, Bioanalytical Method Validation, May 2001, Section VI. Application of Validated Method to Routine Drug Analysis. Once the analytical method has been validated for routine use, its accuracy and precision should be monitored regularly to ensure that the method continues to perform satisfactorily. To achieve this objective, a number of QC samples are prepared separately and should be analyzed with processed test samples at intervals based on the total number of samples. The QC samples are run in duplicate at three concentrations (one near the lower limit of quantification (LLOQ) (i.e., 3×LLOQ), one in midrange, and one close to the high end of the range) and should be incorporated in each assay run. The number of QC samples (in multiples of three) will depend on the total number of samples in the run. The results of the QC samples provide the basis of accepting or rejecting the run. At least four of every six QC samples should be within 15% of their respective nominal value. Two of the six QC samples may be outside the 15% of their respective nominal value, but not both at the same concentration.

The QC samples must cover the high, middle, and low ranges of both standard curves. The QC samples are designed to closely simulate the actual concentrations of labeled compounds found in patient serum over the time course of the testing. The [24-$^{13}$C]-CA concentration is very high at the early time point and falls exponentially to medium and low concentrations. The [2,2,4,4-$^2$H]-CA concentration is very low at the early time point, rises to its highest value in the middle time points and then falls to a medium concentration.

Methods

In one embodiment, the STAT test methods are used for the early detection of undiagnosed liver disease. In certain aspects, the STAT test methods disclosed herein are used to detect early stage liver disease and accurately monitor the progression of liver disease. Early detection with a test such as STAT leads to early intervention when it can be most effective and can reduce healthcare costs and greatly lower morbidity and mortality.

In another aspect, if the STAT test result for a patient is above a threshold value, the patient will undergo the FLOW and/or SHUNT tests are used in conjunction with the STAT test. The FLOW and SHUNT tests can be used to accurately track liver disease. Patients attempting to modify their diet and lifestyle can see even small positive effects in a relatively short timeframe encouraging them to persevere. Physicians can track their patients and manage their care more effectively. Rapidly and accurately evaluating the efficacy of new drugs and therapies will greatly accelerate their development.

In one aspect, the STAT test can be administered to any patient. In various specific aspects, the STAT test can be administered to a patient diagnosed, or suspected of having, NAFLD, PSC, hepatitis C, hepatitis B, alcoholic liver disease, and/or cholestatic disorders.

In further aspects, it is contemplated that the methods of the disclosure, can be used in conjunction with FLOW and SHUNT tests (oral cholate clearance and cholate shunt) for a number of clinical applications, for example, selection of patients with chronic hepatitis B who should receive antiviral therapy; assessing the risk of hepatic decompensation in patients with hepatocellular carcinoma (HCC) being evaluated for hepatic resection; identifying a subgroup of patients on waiting list with low MELD (Model for End-stage Liver Disease score) who are at-risk for dying while waiting for an organ donor; as an endpoint in clinical trials; replacing liver biopsy in pediatric populations; tracking of allograft function; measuring return of function in living donors; and measuring functional impairment in cholestatic liver disease (PSC, Primary Sclerosing Cholangitis).

Figure 5:
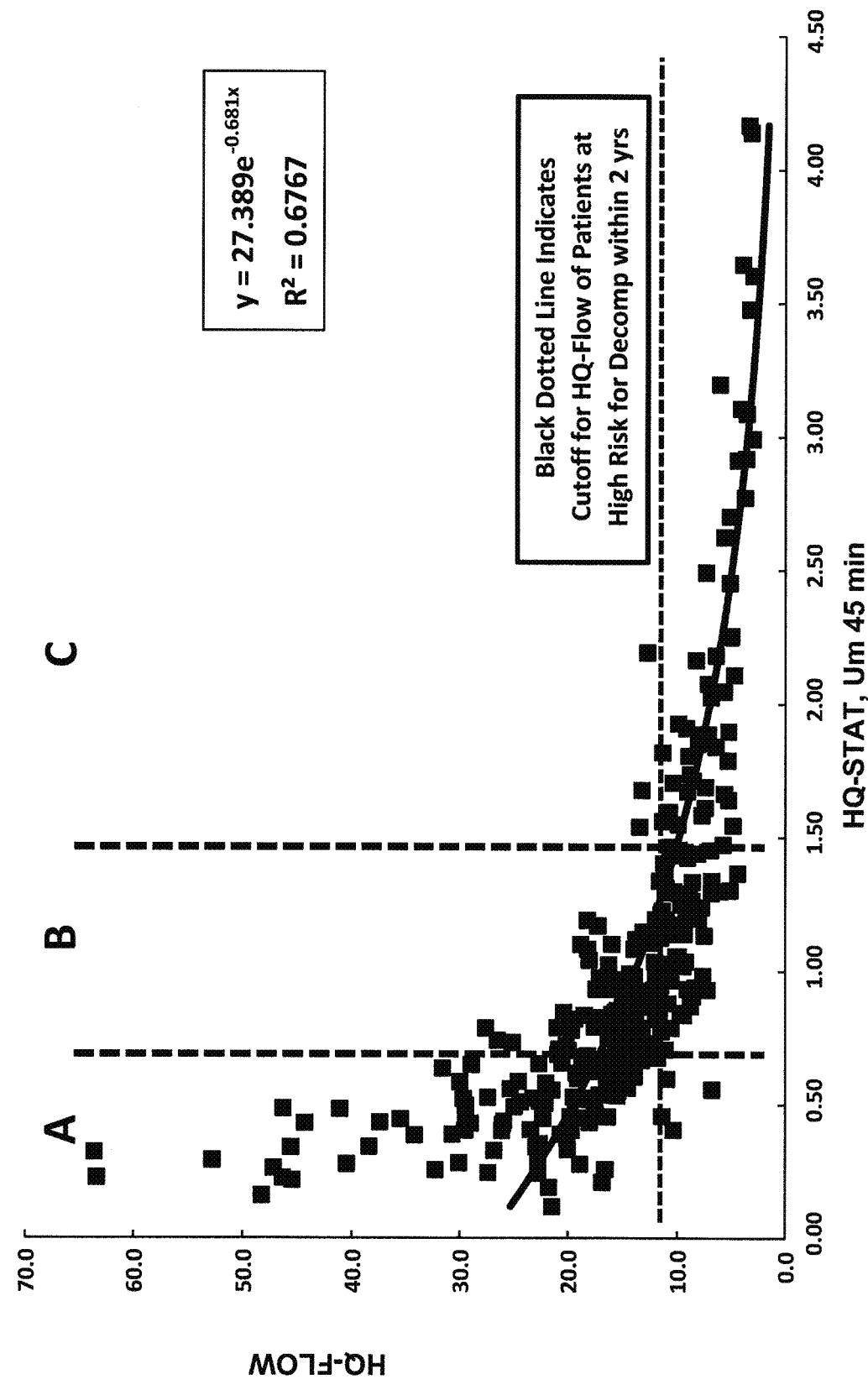
FIG. 5 shows cutoff values and correlation of the herein disclosed STAT test (uM) results at a single time point of 45 minutes after oral administration of 4D-cholate ([2,2,4,4-$^2$H]-Cholic Acid) when compared to FLOW test of portal circulation at 5 time points over 90 minutes following oral administration of 4D cholate. The horizontal dotted line indicates the cutoff (<9.5 ml/min/kg) for FLOW patients at high risk for decompensation within 2 years of test. The vertical dotted lines indicate cutoffs for three STAT result ranges A (low risk), B (intermediate risk) and C (high risk).

In a specific aspect, the methods of the disclosure can be used repeatedly over time as a predictor of clinical outcome. For example, FIG. 5 shows cutoffs and correlation of STAT test (uM) results at a single time point of 45 minutes after oral administration of 4D-cholate when compared to FLOW test of portal circulation at 5 time points over 90 minutes following oral administration of 4D cholate. The horizontal dotted line indicates the cutoff (<9.5 ml/min/kg) for FLOW patients at high risk for decompensation within 2 years of test. The vertical dotted lines indicate cutoffs for three result ranges A, B and C.

In one embodiment, the herein disclosed STAT screening methods can be used in conjunction with FLOW and SHUNT tests (oral cholate clearance and cholate shunt) to monitor hepatic blood flow and hepatic function in an individual patient. A known population of patients is used to establish various cutoff values for the STAT, single-point screening test at a particular selected time point for drawing the single blood sample following oral administration of the distinguishable cholate.

Statistical correlation of the STAT test results from the known patient population compared to FLOW or SHUNT test results is established. In one aspect, FIG. 5 shows cutoffs and correlation of STAT test (uM) results at a single time point of 45 minutes after oral administration of 4D-cholate when compared to FLOW test of portal circulation at 5 time points over 90 minutes following oral administration of 4D cholate. The horizontal dotted line indicates the cutoff (<9.5 ml/min/kg) for FLOW patients at high risk for decompensation within 2 years of test. The vertical dotted lines indicate cutoffs for three result ranges A, B and C.

In another aspect, the STAT test result for an individual patient is compared to the established cutoff values.

Figure 6:
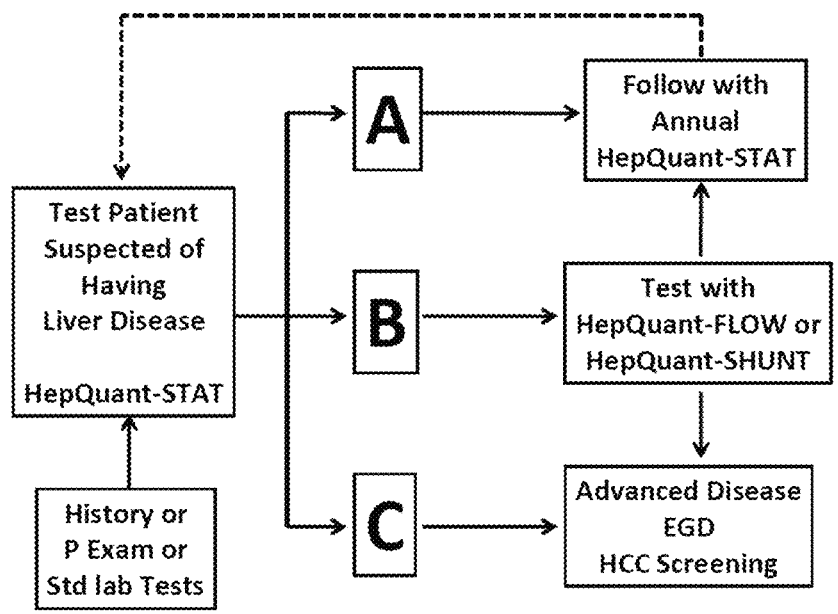
FIG. 6 illustrates clinical application of the STAT test for a patient suspected of having liver disease. For example, a 45 minute STAT test result falling within the range of about 0 to about 0.6 uM ("A" range) is likely to be predictive that the FLOW test result will also fall within the normal range for portal circulation. The patient with a STAT test result falling within the A range can be followed, for example, by use of an annual STAT test. A STAT test result falling within the range of about 0.6 uM to about 1.50 uM ("B" range) is likely to be predictive that the FLOW test result will fall within a compromised range for portal circulation. The patient with a STAT test result falling within the B range should be further evaluated, for example, with the FLOW or SHUNT tests, for assessment of portal circulation and cholate clearances and shunt, respectively. A STAT test result falling above about 1.50 uM (C range) is likely to be predictive of advanced disease. The patient with a STAT test result falling within the C range should be further evaluated, for example, by either additional testing with FLOW or SHUNT or by clinical screening procedures such as EGD (upper endoscopy, esophagogastroduodenoscopy) for varices or radiologic imaging (ultrasonography (US), computed tomography (CT), magnetic resonance imaging (MM)) for HCC (hepatocellular carcinoma).

FIG. 6 illustrates one aspect of a clinical application of the STAT test for a patient suspected of having liver disease. A STAT test result from a patient falling within the range of about 0 to about 0.6 uM ("A" range) is likely to be predictive that the FLOW test result will also fall within the normal range for portal circulation. The patient with a STAT test result falling within the A range can be followed, for example, by use of an annual STAT test. A STAT test result falling within the range of about 0.6 uM to about 1.50 uM ("B" range) is likely to be predictive that the FLOW test result will fall within a compromised range for portal circulation. The patient with a STAT test result falling within the B range should be further evaluated, for example, with the FLOW or SHUNT tests, for assessment of portal circulation and cholate clearances and shunt, respectively. A STAT test result falling above about 1.50 uM ("C" range) is likely to be predictive of advanced disease. The patient with a STAT test result falling within the C range should be further evaluated, for example, by EGD (upper endoscopy, esophagogastroduodenoscopy) and HCC (hepatocellular carcinoma) screening.

Figure 7:
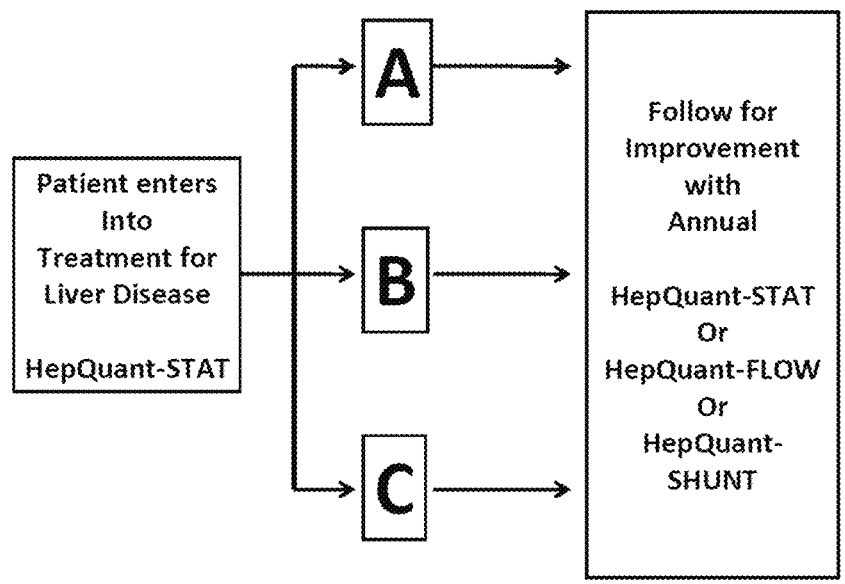
FIG. 7 illustrates clinical application of the STAT test for a patient entering treatment for liver disease. The patient can be monitored periodically for improvement or disease progression. For example, depending on the STAT test result, the patient can be followed for quantitative improvement with annual STAT, FLOW or SHUNT tests.

In another aspect, the STAT test is used to monitor a patient periodically for improvement or liver disease progression. FIG. 7 illustrates clinical application of the STAT test for a patient entering treatment for liver disease. The patient can be monitored periodically for improvement or disease progression. For example, depending on the STAT test result, the patient can be followed for quantitative improvement with annual STAT, FLOW or SHUNT tests.

In another aspect, the STAT test can be used to screen and assess disease severity in a patient diagnosed or suspected of having PSC. STAT showed significant differences between healthy controls and patients with mild disease, and those with PHTN and decompensation (ascites or variceal bleeding), as shown in FIG. 14. The simple and convenient STAT test can be used as a screen to direct patients to the more elaborate FLOW and SHUNT tests shown in FIGS. 12 and 13, respectively. The SHUNT test was demonstrated to significantly differentiate between each subgroup, distinguishing PSC patients with mild disease from healthy controls, and also differentiating the cohorts with and without PHTN, and the group with PHTN from the group with a history of ascites or variceal bleeding, as in FIG. 13.

Definitions and Acronyms

As used herein, "a" or "an" may mean one or more than one of an item.

As used herein "clearance" may mean the removing of a substance from one place to another.

As used herein the specification, "patient", "subject" or "subjects" may include but are not limited to mammals such as humans or mammals for example dogs, cats, ferrets, rabbits, pigs, horses, cattle to birds, or reptiles. The acronym "HALT-C" refers to the Hepatitis C Antiviral Long-term Treatment against Cirrhosis trial. The HALT-C trial was a large, prospective, randomized, controlled trial of long-term low dose peg interferon therapy in patients with advanced hepatitis C who had not had a sustained virologic response to a previous course of interferon-based therapy. An NIH-sponsored Hepatitis C Antiviral Long-Term Treatment against Cirrhosis (HALT-C) Trial examined whether long-term use of antiviral therapy (maintenance treatment) would slow the progression of liver disease. In noncirrhotic patients who exhibited significant fibrosis, effective maintenance therapy was expected to slow or stop histological progression to cirrhosis as assessed by serial liver biopsies. However, tracking disease progression with biopsy carries risk of complication, possibly death. In addition, sampling error and variation of pathologic interpretation of liver biopsy limits the accuracy of histologic assessment and endpoints. The histologic endpoint is less reliable because advanced fibrosis already exists and changes in fibrosis related to treatment or disease progression cannot be detected. Thus, standard endpoints for effective response to maintenance therapy in cirrhotic patients are prevention of clinical decompensation (ascites, variceal hemorrhage, and encephalopathy) and stabilization of liver function as measured clinically by Childs-Turcotte-Pugh (CTP) score. However, clinical endpoints and CTP score were known to be insensitive parameters of disease progression. Dual isotope techniques employing distinguishable cholates were exploited in development of the SHUNT test and used in conjunction with the HALT-C trial.

The term "SHUNT test" refers to a previously disclosed QLFT (quantitative liver function test) used as a comprehensive assessment of hepatic blood flow and liver function. The SHUNT test is used to determine plasma clearance of orally and intravenously administered cholic acid in subjects with and without chronic liver disease. In the SHUNT test, at least 5 blood samples are analyzed which have been drawn from a patient at intervals over a period of at least about 90 minutes after oral and intravenous administration of differentiable cholates. Analysis of samples for stable isotopically labeled cholates is performed by, e.g., GC-MS, following sample derivitization, or LC-MS, without sample derivitization. The ratio of the AUCs of orally to intravenously administered cholic acid, corrected for administered doses, defines cholate shunt. The cholate shunt can be calculated using the formula: $AUC_{oral}/AUC_{iv} \times Dose_{iv}/Dose_{oral} \times 100\%$, wherein $AUC_{oral}$ is the area under the curve of the serum concentrations of the orally administered cholic acid and $AUC_{iv}$ is the area under the curve of the intravenously administered cholic acid. The SHUNT test is disclosed in Everson et al., US2008/0279766, Methods for Diagnosis and Intervention of Hepatic Disorders, filed Jan. 26, 2006, which is incorporated herein by reference. These studies demonstrated reduced clearance of cholate in patients who had either hepatocellular damage or portosystemic shunting.

The SHUNT test allows measurement of first-pass hepatic elimination of bile acids from the portal circulation. Flow-dependent, first pass elimination of bile acids by the liver ranges from 60% for unconjugated dihydroxy, bile acids to 95% for glycine-conjugated cholate. Free cholate, used herein has a reported first-pass elimination of approximately 80% which agrees closely with previously observed first pass elimination in healthy controls of about 83%. After uptake by the liver, cholic acid is efficiently conjugated to either glycine or taurine and secreted into bile. Physicochemically cholic acid is easily separated from other bile acids and bile acid or cholic acid conjugates, using chromatographic methods.

The acronym "IV" or "iv" refers to intravenous.

The acronym "PO" refers to per oral.

The acronym "PHM" refers to perfused hepatic mass.

The acronym "SF" refers to shunt fraction, for example, as in cholate SF.

The acronym "ROC" refers to receiver operating characteristic. The ROC curve is a graphical plot which illustrates performance of a binary classifier system as its discrimination threshold is varied. It is created by plotting the fraction of true positives out of the positives (TPR=true positive rate) vs. the fraction of false positives out of the negatives (FPR=false positive rate), at various threshold settings. Sensitivity is the probability of a positive test result, or of a value above a threshold, among those with disease. Sensitivity is defined as the true positive rate (TPR): TPR=TP/P=TP/(TP+FN). False positive rate (FPR) is FPR=FP/N=FP/(FP+FN). Accuracy (ACC) is defined as ACC=(TP+TN)/(P+N). Specificity is the probability of a negative test result, or a value below a threshold, among those without disease. Specificity (SPC), or true negative rate (TN) is defined as SPC=TN/N=TN/(FP+TN)=1−FPR. Positive prediction value (PPV) is defined as: PPV=TP/(TP+FP). Negative predictive value (NPV) is defined as NPV=TN/(TN+FN). The c-statistic is the area under the ROC curve, or "AUROC" (area under receiver operating characteristic curve) and ranges from 0.5 (no discrimination) to a theoretical maximum of 1(perfect discrimination).

The term "oral cholate clearance" ($Cl_{oral}$) refers to clearance of an orally administered cholate compound. Oral cholate clearance is used as a measure of portal blood flow. Orally administered cholic acid is absorbed across the epithelial lining cells of the small intestine, bound to albumin in the portal blood, and transported to the liver via the portal vein. Approximately 80% of cholic acid is extracted from the portal blood in its first pass through the liver. Cholic acid that escapes hepatic extraction exits the liver via hepatic veins that drain into the vena cava back to the heart, and is delivered to the systemic circulation. The area under the curve (AUC) of peripheral venous concentration versus time after oral administration of cholic acid quantifies the fraction of cholic acid escaping hepatic extraction and defines "oral cholate clearance".

The term "FLOW test" refers to oral cholate clearance (portal hepatic filtration rate; portal HFR) used as a measure of portal blood flow, or portal circulation, obtained from analysis of at least 5 blood samples drawn from a patient over a period of, for example, about 90 minutes after oral administration of a differentiable cholate.

The term "STAT test" refers to an estimate of portal blood flow by analysis from one patient blood sample drawn at a defined period of time following oral administration of a differentiable cholate. In one aspect, the STAT test refers to analysis of a single blood sample drawn at a specific time point after oral administration of a differentiable cholate. In one specific aspect, the STAT test is a simplified convenient test intended for screening purposes that can reasonably estimate the portal blood flow (estimated flow rate) from a single blood sample taken 60 minutes after orally administered deuterated-cholate.

The term "intravenous cholate clearance" ($Cl_{iv}$) refers to clearance of an intravenously administered cholate compound. Intravenously administered cholic acid, bound to albumin, distributes systemically and is delivered to the liver via both portal venous and hepatic arterial blood flow. The AUC of peripheral venous concentration versus time after intravenous administration of cholic acid is equivalent to 100% systemic delivery of cholic acid. The ratio of the AUCs of orally to intravenously administered cholic acid, corrected for administered doses, defines cholate shunt.

The term "Quantitative Liver Function Test" (QLFT), refers to assays that measure the liver's ability to metabolize or extract test compounds, can identify patients with impaired hepatic function at earlier stages of disease, and possibly define risk for cirrhosis, splenomegaly, and varices. One of these assays is the cholate shunt assay where the clearance of cholate is assessed by analyzing bodily fluid samples after exogenous cholate has been taken up by the body.

The term "Ishak Fibrosis Score" is used in reference to a scoring system that measures the degree of fibrosis (scarring) of the liver, which is caused by chronic necroinflammation. A score of 0 represents no fibrosis, and 6 is established fibrosis. Scores of 1 and 2 indicate mild degrees of portal fibrosis; stages 3 and 4 indicate moderate (bridging) fibrosis. A score of 5 indicates nodular formation and incomplete cirrhosis, and 6 is definite cirrhosis.

The term "standard sample" refers to a sample with a known concentration of an analyte used for comparative purposes when analyzing a sample containing an unknown concentration of analyte.

The term "Chronic Hepatitis C" (CHC) refers to a chronic liver disease caused by viral infection and resulting in liver inflammation, damage to the liver and cirrhosis. Hepatitis C is an infection caused by a blood-borne virus that attacks the liver and leads to inflammation. Many people infected with hepatitis C virus (HCV) do not exhibit symptoms until liver damage appears, sometimes years later, during routine medical tests.

The term "Alcoholic SteatoHepatitis" (ASH) refers to a chronic condition of inflammation of the liver which is caused by excessive drinking. Progressive inflammatory liver injury is associated with long-term heavy intake of ethanol and may progress to cirrhosis.

The term "Non-Alcoholic SteatoHepatitis" (NASH) refers to a serious chronic condition of liver inflammation, progressive from the less serious simple fatty liver condition called steatosis. Simple steatosis (alcoholic fatty liver) is an early and reversible consequence of excessive alcohol consumption. However, in certain cases the fat accumulation can be associated with inflammation and scarring in the liver. This more serious form of the disease is termed non-alcoholic steatohepatitis (NASH). NASH is associated with a much higher risk of liver fibrosis and cirrhosis than NAFLD. NAFLD may progress to NASH with fibrosis cirrhosis and hepatocellular carcinoma.

The term "Non-Alcoholic Fatty Liver Disease" (NAFLD) refers to a common chronic liver disease characterized in part by a fatty liver condition with associated risk factors of obesity, metabolic syndrome, and insulin resistance. Both NAFLD and NASH are often associated with obesity, diabetes mellitus and asymptomatic elevations of serum ALT and gamma-GT. Ultrasound monitoring can suggest the presence of a fatty infiltration of the liver; differentiation between NAFLD and NASH, typically requires a liver biopsy.

The term "Primary Sclerosing Cholangitis" (PSC) refers to a chronic liver disease caused by progressive inflammation and scarring of the bile ducts of the liver. Scarring of the bile ducts can block the flow of bile, causing cholestasis. The inflammation can lead to liver cirrhosis, liver failure and liver cancer. Chronic biliary obstruction causes portal tract fibrosis and ultimately biliary cirrhosis and liver failure. The definitive treatment is liver transplantation. Indications for transplantation include recurrent bacterial cholangitis, jaundice refractory to medical and endoscopic treatment, decompensated cirrhosis and complications of portal hypertension (PHTN). PSC progresses through chronic inflammation, fibrosis/cirrhosis, altered portal circulation, portal hypertension and portal-systemic shunting to varices-ascites and encephalopathy. Altered portal flow is an indication of clinical complications.

Other definitions are provided throughout the specification.

Computer/Processor

The detection, prognosis and/or diagnosis method employed in the STAT test can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such as the system interpreting, for example, the LC-MS or GC-MS data, and provides an output to an output device such as a printer, display, network interface, or data storage device. Input device, for example a network interface, receives an input comprising detection of distinguishable cholate compound measured from a processed blood or serum sample described herein and quantification of those compounds. The output device provides an output such as a display, including one or more numbers and/or a graph depicting the detection and/or quantification of the compounds.

Computer system is coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

In embodiments, a method for selecting a treatment for a subject that has an abnormal level of distinguishable cholate compound in a blood or serum sample drawn at a single time point following oral administration comprises calculating an output score, using a computing device, by inputting the distinguishable cholate compound level into a function that provides a predictive relationship between cholate level and outcome, for subjects having a liver disease or disorder; and displaying the output score, using a computing device. In embodiments, distinguishable cholate compound in the sample is converted by using an equation into an estimated portal flow rate (mL/min/kg) in the subject. In embodiments, the equation is y=0.9702x+0.0206, where x is the log Hepquant FLOW and y is LOG Hepquant STAT. In embodiments, the method further comprises determining whether the output score is greater than, or equal to, or less than a cutoff value, using a computing device; and displaying whether the subject is likely to experience a clinical outcome if the output score is greater than, or equal to, or less than a cutoff value.

In embodiments, a computing device, comprises a processing unit; and a system memory connected to the processing unit, the system memory including instructions that, when executed by the processing unit, cause the processing unit to: calculate a level of distinguishable cholate compound from a single blood sample from a subject into a function that provides a predictive relationship between distinguishable cholate level of the subject having a liver disease or dysfunction; and display the output score. In embodiments, the system memory includes instructions that when executed by the processing unit, cause the processing unit to determine whether the output score is greater than or equal to or less than a cutoff value; and displaying whether the subject is likely to experience a clinical outcome if the output score is greater than or equal to the cutoff value.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples are included to demonstrate preferred embodiments.

Example 1. Estimating Portal Flow from a Single Blood Draw

Figure 8:
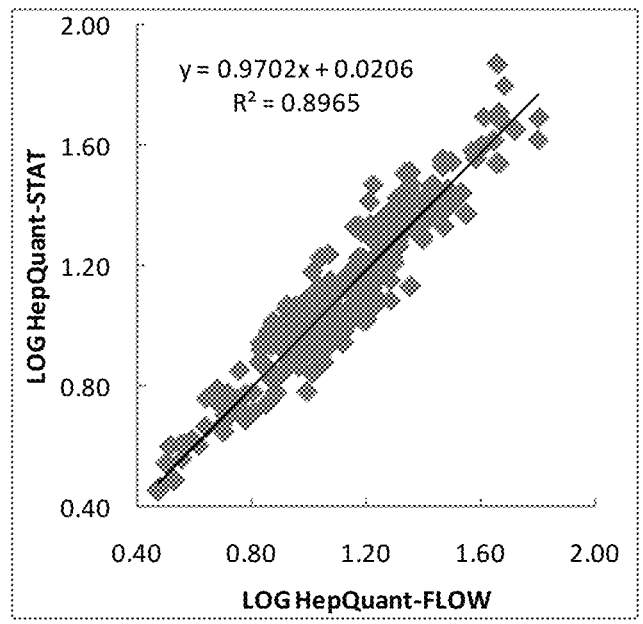
FIG. 8 shows the accuracy and correlation ($R^2$=0.8965) of the 60 minute STAT test relative to the FLOW test from early CHC patients and the equation for interconverting the log STAT and log FLOW values to obtain an estimated flow rate.

The individual time point serum cholate concentrations from the FLOW and SHUNT tests in HALT-C and Early CHC studies were carefully analyzed and differences at 45, 60, and 90 minutes were found to be highly significant (p <0.005). The concentration at 60 minutes had the best correlation ($r^2$=0.8) with the portal flow. An equation was derived that could transform the concentration (uM) at 60 min into an estimated portal flow (mL/min/kg) with 85% accuracy of the 5 point FLOW method. This led to the development of the STAT test, in which, in one embodiment, the patient drinks an oral dose of distinguishable cholate compound, e.g., deuterated-cholate, and gives a single blood sample after 1 hour. The accuracy of the STAT test relative to the FLOW test is shown in FIG. 8.

Example 2. Efficacy of STAT (Estimated Portal Flow) in Detecting Hepatic Dysfunction In the Early CHC study healthy controls had a portal flow of 34±14 ml/min/kg (mean±SD). Hepatic dysfunction was defined as a portal flow more than 1 SD below the control mean, a flow <20 ml/min/kg. In the early CHC group, about ½ the patients exhibited hepatic dysfunction. The estimated portal flows in the early CHC patients were calculated from the equation shown in FIG. 8 using their 60 min serum cholate level. The estimated flow could detect hepatic dysfunction with a sensitivity of 90%, a specificity of 85%, a positive predictive value (PPV) of 82%, and a negative predictive value (NPV) of 92%. These preliminary results demonstrate that a single blood sample after an oral cholate dose could be used to detect hepatic dysfunction in early stage CLD.

Furthermore, in the Early CHC study we analyzed the potential impact of STAT if used as a screening test. Currently adults are screened for liver disease in the primary care setting by ALT. In our analysis of the Early CHC study we found that addition of STAT to ALT could improve detection of patients with chronic hepatitis C. In early stage patients, ALT was abnormal in only 34%, STAT was abnormal in 48%, and 65% of the patients had either abnormal ALT or STAT. Screening with combination of ALT and STAT would double the detection rate for patients with liver disease due to chronic hepatitis C. Of course, when used in such a strategy, STAT would also detect patients with liver diseases other than chronic hepatitis C as well.

STAT also has test cutoffs that correlate with advanced liver disease. In patients with chronic hepatitis C and in patients with the chronic cholestatic liver disease, primary sclerosing cholangitis, STAT result with estimated FLOW of <10 mL/(kg min) correlated with risk for liver decompensation or clinical complications. In this situation, STAT would reflex to either FLOW or SHUNT to provide precise quantification of the portal circulation.

Example 3. Procedure for Performance of an Exemplary STAT Test

Supplies

PO (Per Oral) Test Compounds $^2$H4-Cholate ([2,2,4,4-$^2$H]-Cholic Acid, 40 mg) (e.g. CDN Isotopes).
Sodium bicarbonate (e.g. 600 mg).

Patient Testing Supplies

Serum/plasma transfer tubes and labels.
10 cc syringe for drawing blood sample.
7 cc red top and 7 cc gray top vacutainer tubes for serum sample collection.
Needle discard bucket
A drinking substance such as apple or grape juice for diluting oral test compounds.

Exemplary Test Compound Preparation

One exemplary solution of an oral composition may contain 2,2,4,4-$^2$H-Cholate, and Sodium bicarbonate (e.g. 40 mg, and 600 mg, respectively). In one exemplary method, the day before the test, water can be added to about the 10 cc mark on a tube containing the oral test compounds to obtain the Oral Test Solution. Cap tube tightly and shake to mix. Swirl contents to get all the powder granules down into the water.

On the test day pour dissolved Oral Test Solution into a container such as a urine cup. Rinse tube into urine cup with about 10 mls water. Prior to beginning the test, add a diluting liquid such as grape or apple juice (not citrus juice) to about the 40 ml mark on the urine cup containing the Oral Test Solution. Swirl gently to mix; do not shake or stir, or mixture may foam out of container. Have extra juice on hand for rinse.

Testing Procedure

In one exemplary method the following procedure will be used. Optionally collect baseline serum sample (see Sample Collection) before test compound is administered.

Administration of Test Compounds

Start timer. Record T=0.0—have patient drink oral solution of cholate and juice. Rinse cup with a little more juice and have patient drink rinse. Record timer time.

Sample Collection

Blood

Collect the intravenous blood sample from the patient at 60 minutes post cholate administration. Record timer time.
Process blood samples and perform sample analysis by HPLC/MS (as outlined below for FLOW and SHUNT); or by GC/MS to determine the concentration of distinguishable cholate in the blood sample. The sample test result for a given patient at a specific date/time point can be compared to cutoff values established from, e.g., a control group, or alternatively each patient may serve as his/her own control over time.

Example 4. Procedure for Performance of SHUNT and FLOW Assays with Analysis by HPLC-MS Performance of FLOW (Oral Cholate Clearance Test) and SHUNT (Cholate Shunt Test) assays are disclosed in US 2010/0055734 and US 2008/0279766, each of which is incorporated herein by reference.

Collection and Processing of Samples

Reagents and Supplies

The following reagents and supplies are utilized in the Cholate Shunt and Cholate Clearance Test procedures. If the patient is undergoing only the oral cholate clearance test, the IV Solution and 25% Human Albumin for injection are omitted.
IV Solution—20 mg 24-$^{13}$C-Cholic Acid in 5 cc 1 mEq/ml Sodium Bicarbonate
PO test compounds 2,2,4,4-$^2$H (40 mg) and Sodium Bicarbonate (600 mg)
25% Human Albumin for injection (5 ml) to be added to 24-$^{13}$C-Cholic Acid solution.
IV supplies, including 250 mls NS, indwelling catheter, 3-way stopcock.
10 cc syringes for administering IV test compounds
7 cc red top tubes for sample collection
3 ml crovials for serum storage
Needle discard bucket
Apple or Grape (non-citrus) juice for oral test compounds
Timer
Centrifuge
Transfer pipets Patient Preparation It is ascertained that the patient has no allergic reaction to latex. It is further ascertained that the patient has had nothing to eat or drink (NPO), except water, since midnight the night before the test day. The patient height and weight are measured and recorded. The patient is fitted with an IV with a three-way stopcock and normal saline to keep open (NS TKO) is placed before the test begins.

Cholate Compound Stock Solutions

Test Compound Preparation

The Oral Solution is utilized for either or both of the oral cholate clearance test and/or the cholate shunt assay. The oral solution including 2,2,4,4-$^2$H-Cholic acid (40 mg) and Sodium Bicarbonate (600 mg) is dissolved in about 10 cc water 24 hours prior to testing by mixing vigorously. The solution is stored in either the refrigerator or at room temperature. Just prior to administration, grape or apple (non-citrus) juice is added to the mixture. The juice solution is mixed well and poured into cup for patient to drink. The cup is rinsed with extra juice which is administered to the patient.

The IV Solution is utilized for either or both of the IV cholate clearance test and/or the cholate shunt assay. A formulation of 20 mg Cholic Acid-24-$^{13}$C in 5 cc 1 mEq/ml Sodium Bicarbonate is prepared by pharmacy staff. The Test dose is 20 mg Cholic Acid-24-$^{13}$C in 10 cc diluent. If vial is frozen, it is allowed to thaw completely. Just prior to beginning the test, the Cholic Acid-24-$^{13}$C solution is mixed with albumin as follows (this method prevents loss of test compound during mixing process). Draw up all of 24-$^{13}$C-Cholic Acid solution (about 5 cc) in a 10 cc syringe. Draw up 5 cc albumin in another 10 cc syringe. Detach needle from the 24-$^{13}$C-cholate syringe and attach a 3-way stopcock. Detach needle from albumin syringe and inject albumin through stopcock into 24-$^{13}$C Cholate syringe. Draw a little air into the bile acid/albumin syringe and mix solutions gently by inverting syringe several times. Expel air.

Test Compound Administration

Collect baseline samples before test compounds are given. The time these specimens are collected should be recorded on sample collection record sheet. Administration of test compounds is performed as follows. Start timer. Record 24 hour clock time as T=0. Record time. At T=1-3 minutes administer oral compounds. Have the patient drink the oral solution and juice. Rinse cup with more juice and have patient drink rinse. Record timer time. At T=4-5 minutes-using the 3-way stopcock administer the IV push of 20 mgs $^{13}$C Cholic acid in 5 mls 25% Human Albumin. Record timer time. Return line to NS through 3-way stopcock.

Specimen Collection

Collect all samples via the 3-way stopcock with 0.5 ml discard before each sample to prevent dilution or cross-contamination of samples. Collect 5 ml red tops at the following times. (T=timer time).
 a. T=10 minutes, collect 5 minute, record timer time;
 b. T=25 minutes, collect 20 minute, record timer time;
 c. T=50 minutes, collect 45 minute, record timer time;
 d. T=65 minutes, collect 60 minute, record timer time;
 e. T=95 minutes, collect 90 minute, record timer time.

Specimen Handling

Red top tubes are allowed to clot at room temperature for at least 30 minutes. All blood tubes are spun for 10 minutes at 3000 rpm. Serum is removed to properly labeled vials and frozen at −20° C. until samples are transported.

Preparation of Cholate Compound Stock Solutions

Accurate determination of cholate clearances and shunt is dependent on accurate calibration standards. Concentrations of cholic acid compounds in stock solutions must be accurate and reproducible. Very accurate (error<0.5%) portions of the cholic acid powders are weighed and glass weighing funnels and washes of 1 M NaHCO$_3$ are used to ensure quantitative transfer of the powder to the flask. Volumetric flasks are used to ensure accurate volumes so that the final concentrations of the primary stock solutions are accurate. Calibrated air displacement pipettes are used to dispense accurate volumes of the primary stock solutions that are brought to full volume in volumetric flasks to prepare secondary stock solutions that are also very accurate. Secondary stock solutions are used to prepare the standard curve samples, accuracy and precision samples, recovery samples, quality control samples, selectivity samples, and stability samples as described in the appropriate SOPs.

The following reagents are required.
1 M NaHCO$_3$
0.1 M NaHCO$_3$
0.1 M NaHCO$_3$/2% BSA
Methanol, LCMS grade
Water, CLRW grade (Clinical Laboratory Reagent Water)
Cholic Acid, purity 98%
Chenodeoxycholic Acid, purity 98%
[24-$^{13}$C]-Cholic Acid, 99 atom % $^{13}$C
[2,2,4,4-$^2$H]-Cholic Acid, 98 atom % $^2$H.

All primary stock solutions are prepared at a concentration of 250 uM using Table 2 below.

TABLE 2

Cholate compound primary stock solutions.

|  | cholic acid | 13-C cholic acid | 4-D cholic acid | chenodeoxcholic acid |
|---|---|---|---|---|
| MW | 408.56 | 409.59 | 412.60 | 392.56 |
| purity | 98.0% | 99.0% | 98.0% | 98.0% |
| volume | 100 ml | 100 ml | 100 ml | 100 ml |
| conc | 250 uM | 250 uM | 250 uM | 250 uM |
| weight | 10.42 mg | 10.34 mg | 10.53 mg | 10.01 mg |

Primary stock solutions are prepared separately in 0.1 M NaHCO$_3$ and in methanol as follows. Weigh out the appropriate amount of cholic acid compound (+/−0.05 mg) in a glass weighing funnel. Transfer the powder to a 100 ml volumetric flask. Use either methanol or 0.1M NaHCO$_3$ to rinse any residual powder from the funnel into the flask. Bring to a final volume of 100 ml with methanol and mix well. Label flask with an expiration of 1 month. Store at −20° C.

The unlabeled cholic acid is prepared as a 50 uM internal standard in either MeOH or 0.1 M NaHCO$_3$ as follows. Pipette 2.0 ml of the appropriate 250 uM CA primary standard into a 10 ml volumetric flask. Bring to a total volume of 10 ml with 0.1 M NaHCO$_3$ or methanol and mix well. Label flask with an expiration of 1 year. Store at 4° C.

[24-$^{13}$C]-Cholic Acid secondary stock solutions made in methanol are shown in Table 3. Each secondary stock solution into the appropriate 15 ml glass screw top test tube. Tubes are securely capped and sealed with several layers of parafilm and stored at −20° C.

TABLE 3

[24-$^{13}$C]-Cholic acid secondary stock solutions in methanol.

| final assay concentration uM | Secondary Stocks uM | 250 uM 13C-CA (m) ul | Methanol ml | Total ml |
|---|---|---|---|---|
| 0.20 | B (m) 2.0 | 80 + | 9.92 = | 10.00 |
| 1.00 | D (m) 10.0 | 400 + | 9.60 = | 10.00 |
| 6.00 | F (m) 60.0 | 2400 + | 7.60 = | 10.00 |
|  |  | 2880 | 27.12 | 30.00 |

[2,2,4,4-$^2$H]-Cholic Acid secondary stock solutions made in methanol are shown in Table 4. Each secondary stock solution into the appropriate 15 ml glass screw top test tube. Tubes are securely capped and sealed with several layers of parafilm and stored at −20° C.

TABLE 4

[2,2,4,4-$^2$H]-Cholic acid secondary stock solutions in methanol.

| final assay concentration uM | Secondary Stocks uM | 250 uM 4D-CA (m) ul | Methanol ml | Total ml |
|---|---|---|---|---|
| 0.30 | I (m) 3.0 | 120 + | 9.88 = | 10.00 |
| 1.00 | K (m) 10.0 | 400 + | 9.60 = | 10.00 |
| 3.00 | L (m) 30.0 | 1200 + | 8.80 = | 10.00 |
|  |  | 1720 | 28.28 | 30.00 |

[24-$^{13}$C]-Cholic Acid secondary stock solutions made in 0.1 M NaHCO$_3$ and BSA are shown in Table 5. Each secondary stock solution is transferred into the appropriate 15 ml screw top plastic tube, capped, sealed with several layers of parafilm and stored at 4° C.

TABLE 5

[24-$^{13}$C]-Cholic acid secondary stock solutions in 0.1M NaHCO$_3$ and BSA.

| final assay concentration uM | Secondary Stocks uM | 250 uM 13C-CA ul | 0.1M NaHCO3 ml | 2% BSA ml | Total ml |
|---|---|---|---|---|---|
| 0.10 | A 1.0 | 40 + | 4.96 + | 5.00 = | 10.00 |
| 0.20 | B 2.0 | 80 + | 4.92 + | 5.00 = | 10.00 |
| 0.60 | C 6.0 | 240 + | 4.76 + | 5.00 = | 10.00 |
| 1.00 | D 10.0 | 400 + | 4.60 + | 5.00 = | 10.00 |
| 2.00 | E 20.0 | 800 + | 4.20 + | 5.00 = | 10.00 |
| 6.00 | F 60.0 | 2400 + | 2.60 + | 5.00 = | 10.00 |
| 10.00 | G 100.0 | 4000 + | 1.00 + | 5.00 = | 10.00 |
|  |  | 7960 | 27.04 | 35.00 | 70.00 |

[2,2,4,4-$^2$H]-Cholic Acid secondary stock solutions made in 0.1 M NaHCO$_3$ and BSA are shown in Table 6. Each secondary stock solution is transferred into the appropriate 15 ml screw top plastic tube, capped, sealed with several layers of parafilm and stored at 4° C.

TABLE 6

[2,2,4,4-$^2$H]-Cholic acid secondary stock solutions in 0.1M NaHCO$_3$ and BSA.

| final assay concentration uM | Secondary Stocks uM | 250 uM 4D-CA ul | 0.1M NaHCO3 ml | 2% BSA ml | Total ml |
|---|---|---|---|---|---|
| 0.10 | H 1.0 | 40 + | 4.96 + | 5.00 = | 10.00 |
| 0.30 | I 3.0 | 120 + | 4.88 + | 5.00 = | 10.00 |
| 0.50 | J 5.0 | 200 + | 4.80 + | 5.00 = | 10.00 |
| 1.00 | K 10.0 | 400 + | 4.60 + | 5.00 = | 10.00 |
| 3.00 | L 30.0 | 1200 + | 3.80 + | 5.00 = | 10.00 |
| 5.00 | M 50.0 | 2000 + | 3.00 + | 5.00 = | 10.00 |
|  |  | 3960 | 26.04 | 30.00 | 60.00 |

The secondary stock solutions as prepared above are utilized in preparation of accuracy and precision samples in human serum with unlabeled cholate as an internal standard. The secondary stock solutions are used in preparation of recovery samples with addition of unlabeled cholate as an internal standard.

In order to accurately measure patient liver function with the cholate shunt assay, the two different stable isotope cholate compounds must each be accurately quantified in patient serum. In order to do this, the accuracy, precision, and recovery of each of the two standard curves must be validated over their respective ranges of concentrations.

The accuracy and precision of an assay are assessed by running multiple replica samples at the lower limit of quantification (LLOQ), low, medium, and high range of concentrations. Accuracy is the closeness of the average measured value to the actual value. Precision is the reproducibility of the measured value as indicated by the CV. The recovery is assessed by comparing the detector response of the analyte extracted from serum relative to that of pure analyte measured at low, medium, and high concentrations.

Preparation of Quality Control Samples

The FDA provides guidance as to acceptable levels of accuracy and precision of analytical methods. See, for example, Bioanalytical Method Validation, May 2001, Section VI. Application of Validated Method to Routine Drug Analysis. Once the analytical method has been validated for routine use, its accuracy and precision should be monitored regularly to ensure that the method continues to perform satisfactorily. To achieve this objective, a number of QC samples are prepared separately and should be analyzed with processed test samples at intervals based on the total number of samples. The QC samples are run in duplicate at three concentrations (one near the lower limit of quantification (LLOQ) (i.e., 3×LLOQ), one in midrange, and one close to the high end of the range) and should be incorporated in each assay run. The number of QC samples (in multiples of three) will depend on the total number of samples in the run. The results of the QC samples provide the basis of accepting or rejecting the run. At least four of every six QC samples should be within 15% of their respective nominal value. Two of the six QC samples may be outside the 15% of their respective nominal value, but not both at the same concentration.

The QC samples must cover the high, middle, and low ranges of both standard curves. The QC samples are designed to closely simulate the actual concentrations of labeled compounds found in patient serum over the time course of the testing. The [24-$^{13}$C]-CA concentration is very high at the early time point and falls exponentially to medium and low concentrations. The [2,2,4,4-$^2$H]-CA concentration is very low at the early time point, rises to its highest value in the middle time points and then falls to a medium concentration.

Supplies

The following supplies are utilized to prepare the QC samples used in the Cholate Shunt and Cholate Clearance Test procedures. If the patient samples are undergoing only the oral cholate clearance test, the [24-$^{13}$C]-CA QC samples can be omitted.

Human Serum AB (Gemini Bio-Products #100-512)

Unlabeled Cholate Internal Standard Stock Solution
(IS; 50 uM Cholic Acid in 0.1M NaHCO$_3$)
[24-$^{13}$C]-Cholic Acid and [2,2,4,4-$^2$H]-Cholic Acid
Secondary Stock Solutions in 0.1 M NaHCO$_3$/1% BSA B 2.0 uM [24-$^{13}$C]-CA
D 10.0 uM [24-$^{13}$C]-CA
F 60.0 uM [24-$^{13}$C]-CA
I 3.0 uM [2,2,4,4-$^2$H]-CA
K 10.0 uM [2,2,4,4-$^2$H]-CA
L 30.0 uM [2,2,4,4-$^2$H]-CA
10 ml volumetric flasks
P1000 air displacement pipette and 1 ml tips
New, clean cryovials Procedure for Preparation of Quality Control Samples for Cholate Clearance and Assays The [24-$^{13}$C]-Cholic Acid and [2,2,4,4-$^2$H]-Cholic acid QC samples are prepared as follows. For each set of QC samples, label 3 clean 10 ml volumetric flasks as "QC 1", "QC 2", and "QC 3" as shown in Table 7. Larger volumetric flasks can be used to prepare larger batches. Use 1/10 the nominal volume of the larger flasks as the amount of secondary stock solution to add as indicated below.

TABLE 7

| | QC samples. | |
| --- | --- | --- |
| Tubes | [24-$^{13}$C]-CA | [2,2,4,4-$^2$H]-CA |
| QC1 | 1.00 ml F | 1.00 ml I |
| QC2 | 1.00 ml D | 1.00 ml L |
| QC3 | 1.00 ml B | 1.00 ml K |

Using a P1000, add 1.0 ml of the appropriate [24-$^{13}$C]-CA stock solution and 1.0 ml of the appropriate [2,2,4,4-$^2$H]-CA stock solution to the appropriate flasks as indicated in Table 6. Bring each flask to an exact total of 10.0 ml with human serum. Securely cap each flask and mix well by inversion several times. Label 8 cryovials as "QC 1", 8 as "QC 2", and 8 as "QC 3". Aliquot 1.2 ml of each QC mixture into the appropriate vials. Store the QC samples frozen at −80° C. QC samples have an expiration of 1 year.

High Pressure Liquid Chromatography-Mass Spectroscopy (HPLC-MS) Sample Preparation In order to ensure accurate liver function testing, the labeled cholate test compounds must be isolated and identified from patients' serum samples. Cholate compounds are amphipathic molecules with both hydrophobic and hydrophilic regions. Cholates are also carboxylic acids that can exist in either an uncharged free acid form (cholic acid) or a charged carboxylic acid form (cholate) depending on pH. These properties can be exploited to isolate cholate compounds from serum. The use of HPLC/MS as opposed to GC/MS, allows analysis of cholate without sample derivitization. Alternatively, GC/MS can be used for sample analysis with derivitization by any technique known in the art, for example, by the method of Everson and Martucci, US 2008/0279766, incorporated herein by reference.

Reagents, Supplies and Equipment

The following reagents are prepared and used in the HPLC-MS sample preparation.
Water, CLRW grade (Clinical Laboratory Reagent Water)
Methanol, LCMS grade
Diethyl Ether, ACS grade
Unlabeled Cholic Acid Internal Standard (IS) Primary Stock Solution (50 uM CA in 0.1 M NaHCO$_3$)
Quality Control Samples (prepared as described above)
1.0 N NaOH (dissolve 20 g NaOH in 500 ml water)
0.01 N NaOH (dilute 1.0 N NaOH 1 to 100 with water)
10% Methanol (add 100 ml Methanol to a 1 L cylinder and bring to 1.0 L with water)
90% Methanol (add 900 ml Methanol to a 1 L cylinder and bring to 1.0 L with water)
0.2 N HCl (add 1.0 ml ACS grade Concentrated HCl slowly with stirring to 57.0 ml water)
Mobile Phase (10 mM Ammonium Acetate/60% Methanol)
Disposable 16×100 and 13×100 test tubes
P1000 air displacement pipette and 1 ml tips
P100 air displacement pipette and 0.2 ml tips
Repeater Pipette
Vortex Mixer
SPE cartridges (Bond Elut LRC C18 OH, 500 mg, Varian, Inc.)
Vacuum Manifold
Speed-Vac
Benchtop centrifuge
Speed-Vac vented to fume hood
Bath Sonicator
Repeater Dispensers for water, methanol, 10% methanol, and 90% methanol
Remove patient serum samples and a set of QC samples (2 each of QC1, 2, and 3) from the freezer and allow them to thaw to room temperature. Personal protective equipment (PPE) including lab coat, gloves, eye protection must be worn. All eluates and equipment must be disinfected. Pipettes and tips that come in contact with the sample must be discarded into hazardous waste.

Label a set of test tubes (16×100) for each patient with that patient's initials and the time point code (5 min is 1, 20 min is 2, 45 min is 3, 60 min is 4, 90 min is 5). Using a P1000 pipette, transfer 0.50 ml of patient's serum from the appropriate collection tube into the appropriate test tube.

Label a set of test tubes (16×100) for each QC sample (QC1a, QC1b, QC2a, QC2b, QC3a, QC3b). Using a P1000, transfer 0.50 ml of each QC sample into the appropriate test tube.

Label 2 test tubes (13×100) as STD1 and STD2.

To each patient sample and each QC sample and each STD sample tube, add 50 ul of the Unlabeled Cholic Acid Internal Standard (IS) Primary Stock Solution using a Repeater Pipette.

Set aside the STD tubes for later acidification and ether extraction in step 21.

To each patient sample tube and QC sample tube add 1.0 ml of 0.01 N NaOH with a Repeater pipet and vortex 30 sec.

Label a set of SPE cartridges with one for each patient serum and QC sample to be processed.

In the hood add 5 ml Methanol with a repeater dispenser to each cartridge. This step may be done on a vacuum manifold with high vacuum or by gravity. This wets the resin bed with solvent. Once the top of the liquid reaches the top of the frit add the next solution. Avoid letting the cartridges run dry.

Add 10 ml Water with the repeater dispenser to each cartridge. This equilibrates the resin bed to prepare it for binding cholate compounds. This step may be done on the vacuum manifold on high vacuum or by gravity.

To each SPE cartridge add the appropriate sample. The cholate compounds will bind to the resin bed. To each sample test tube add a 1 ml water rinse with the repeater, vortex, and add this rinse to the appropriate cartridge. Allow the sample to run by gravity for 20 minutes or longer then may use low vacuum≤3 inches Hg to pull sample through.

After the sample has completely entered the resin bed, add 2.5 ml Water to each SPE cartridge with the repeater dispenser. This washes the column resin bed. Use low vacuum≤3 inches Hg.

To each SPE cartridge add 2.5 ml 10% Methanol with the repeater dispenser. This further washes the column resin bed. Use low vacuum≤3 inches Hg.

Label a set of test tubes (13×100) with one for each patient sample and each QC sample.

Place each test tube in a rack and on top place its matching SPE cartridge.

To each SPE cartridge add 2.5 ml 90% Methanol with the repeater dispenser. This elutes the cholate compounds which are collected into the test tubes.

Place the test tubes in the Speed-Vac and centrifuge under vacuum with high heat for 45 min to reduce eluate volume and to remove methanol which interferes with ether extraction.

To each tube from the Speed-Vac and to each of the STD tubes, add 0.5 ml of 0.2 N HCl with the Eppendorf Repeater Pipette and vortex 30 sec. This acidification converts the cholate compounds into their free acid form for ether extraction.

In the fume hood, to each tube add 3 ml of diethyl ether and vortex vigorously for 30 sec. This extracts the free acid form of the cholate compounds into the ether phase.

Centrifuge 5 minutes at a minimum of 5000 rpm to accelerate phase separation.

Label another set of test tubes (13×100) one for each sample.

Carefully collect the upper ether layer and transfer to the new test tubes.

Place the ether extracts in the Speed-Vac vented to the fume hood and centrifuge under vacuum without heat until samples are dry. Alternatively, samples can be dried with a gentle stream of $N_2$ gas.

Add 100 ul Mobile Phase to dried samples, vortex 30 sec and sonicate.

Transfer samples to Agilent 1.5 ml vials and cap.

HPLC/MS Parameters and System Preparation

Reagents, Supplies and Equipment

The following reagents are prepared and used in the HPLC-MS sample analysis.
Water, Clinical Laboratory Reagent Water (CLRW)
Methanol LCMS grade
10 mM Ammonium Acetate water
10 mM Ammonium Acetate methanol
Mobile Phase: 60% 10 mM Ammonium Acetate Methanol/ 40% 10 mM Ammonium Acetate Water
Volumetric flasks, appropriate sizes
Graduated cylinder The following instruments and supplies are used in the HPLC-MS sample analysis.
Calibrated analytical balance
HPLC/MS instrument: Agilent 1100 series Liquid Chromatograph Mass Spectrometer equipped with a G1956A multi-mode source, automatic sampler, HP Chemstation Software or equivalent.
Agilent Eclipse XDB C8, 2.1×100 mm 3.5 um liquid chromatograph column
Solvent Filter Degasser
0.22 μm nylon filters The solvents and mobile phase are each prepared, filtered with a 0.22 μm nylon filter and degassed. Solvents and mobile phase each expire 48 hours after preparation.

The LCMS system is prepared and tuned; the column is stabilized at 40° C. and conditioned by running the mobile phase for 30 min. The samples are loaded to the autosampler. The column flow rate is 0.4 ml/min of isocratic mobile phase buffer; 60% 10 mM Ammonium Acetate Methanol/40% 10 mM Ammonium Acetate Water. 5 microliters of each sample is injected by the autosampler. The MS is run in multimode electrospray (MM-ES) ionization with atmospheric pressure chemical ionization (APCI) ionization. Selected ion monitoring is performed at 407.30, 408.30 and 411.30 m/z. Peaks are integrated by the system software. Three QC samples are assayed with each analytical run. The concentration of the QC samples must fall within 15% accuracy.

Data from selective ion monitoring of either or both intravenous and oral samples are used to generate individualized oral and intravenous clearance curves for the patient. The curves are integrated along their respective valid time ranges and an area is generated for each. Comparison of intravenous and oral chloate clearance curves allows determination of first-pass hepatic elimination or portal shunt. The liver shunt fraction calculated by the formula:

$$\text{ShuntFraction}=[\text{AUC}_{oral}/\text{AUC}_{IV}]*[\text{Dose}_{IV}/\text{Dose}_{oral}]*100\%.$$

wherein AUC represents area under the curve and Dose represents the amount (in mg) of dose administered.

Example 5. NAFLD Testing and Analysis

Clinical Protocol. The deuterated-cholate (product #614149) and $^{13}$C-cholate (product #605883) are purchased from Sigma-Isotec (Saint Louis, Missouri) and dissolved in sodium bicarbonate buffer. The inventor has held the INDs #65121 and 65123 on these compounds since 2002 and reports annually to the FDA. The $^{13}$C-cholate for injection is filtered, tested for sterility and pyrogens, and frozen in aliquots by a research pharmacist. After an overnight fast, each subject will receive an indwelling intravenous catheter and a baseline venous blood sample will be drawn. The subject will drink the deuterated-cholate dose mixed with grape juice, and at the same time, the $^{13}$C-cholate mixed with albumin will be administered IV. At time points of 5, 20, 45, 60, and 90 minutes, venous blood samples will be drawn. After processing to serum, samples will be transferred to the Clinical Testing Laboratory. Each subject will be tested 3 times within a period of 1 month.

Laboratory Analyses. Patient serum samples will be spiked with unlabeled cholate as internal standard and then the cholates will be isolated by SPE and ether extraction. LCMS on C8 and Selected Ion Monitoring (SIM) will be used to quantify the test compounds by the isotope dilution method. All analytical runs will include appropriate standard curves and QC samples. The oral clearance (FLOW test result) and IV clearance will be calculated from the serum concentrations at the 5 time points. The ratio of IV to oral clearance is the SHUNT test result. The oral clearance is estimated from only the 60 minute time point is the STAT test result.

F0-F2 patients were in the normal range in standard laboratory tests. Liver function was not significantly impaired in CHC F0-F2 patients.

The portal circulation was quantified by the clearance of orally administered cholate-d4 (FLOW), the ratio of the clearances of intravenous cholate-$^{13}$C to oral cholate-d4 (SHUNT), and serum cholate-d4 at 60 min (STAT). Labeled cholates were assayed by an LCMS method validated for accuracy and precision. As CHC progresses, FLOW, which assesses the portal blood flow, is reduced while SHUNT, which assesses portal-systemic shunting, is increased. STAT, which uses a single blood sample to infer the impaired FLOW, is also increased.

Results: Within the F0-F2 patient group, 62% had normal ALT, 95% had normal bilirubin, 95% had normal INR, and 71% had normal albumin. All the metabolic tests failed to detect hepatic impairment in F0-F2 patients. However the F0-F2 patients had significantly lower FLOW, higher SHUNT, and higher STAT, as shown in Table 8. STAT was shown to be more sensitive than standard tests in detection of early stage HCV.

TABLE 8

FLOW, STAT and SHUNT Test Results in HCV F0-F2 patients compared to healthy controls.

| Test | Controls (n = 32) | CHC F0-F2 (n = 21) | p value | ROC c-statistic | Cutoff | Sens. | Spec. |
|---|---|---|---|---|---|---|---|
| FLOW (mL/min/kg) | 30 +/− 9 | 20 +/− 6 | 0.00003 | 0.81 | <20.3 | 57% | 88% |
| SHUNT (%) | 19 +/− 5% | 26 +/− 7% | 0.0008 | 0.75 | >25.2% | 52% | 88% |
| STAT (µM) | 0.38 +/− 0.13 | 0.64 +/− 0.13 | 0.0005 | 0.73 | >0.52 | 52% | 91% |

Example 6. Significant Alteration of the Portal Circulation in Over Half of the Chronic HCV Patients with Ishak Fibrosis Stage F0-F2. Establishment of a Cutoff for Identification of a High Risk Subset Approximately 40% of patients with chronic hepatitis C (CHC) have minimal disease as defined by Ishak fibrosis stages F0 to F2. A subset of F0-F2 patients, presumably with hepatic impairment, progress to cirrhosis and clinically decompensate. This study was used to identify the high risk subset by quantifying hepatic impairment using noninvasive quantitative tests.

Methods: Patients with CHC and Ishak F0-F2 (n=21) were recruited from our Hepatology Clinic and compared to healthy control subjects (n=32).

Subjects were placed on a caffeine-free diet and fasted overnight. The next morning caffeine (300 mg), antipyrine (500 mg), and cholate-2,2,4,4-$d_4$ (40 mg) were administered orally; and cholate-24-$^{13}$C (20 mg), galactose (30 g), and lidocaine (0.5 mg/kg) were administered intravenously. Timed samples were: caffeine and antipyrine saliva samples 0-60 hours, MEGX serum samples 15 and 30 minutes, galactose serum samples 20-80 minutes, and cholate serum samples 0-90 minutes.

Figure 9A:
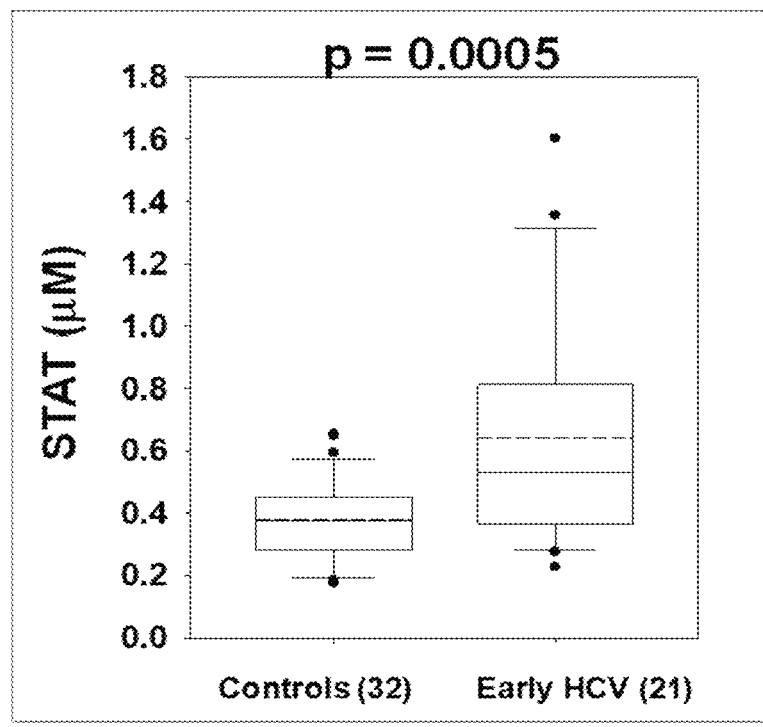
FIG. 9A shows a boxplot for STAT in CHC Ishak fibrosis stage F0-F2 patients compared to healthy controls. STAT is significantly increased in HCV F0-F2 patients compared to controls.
Figure 9B:
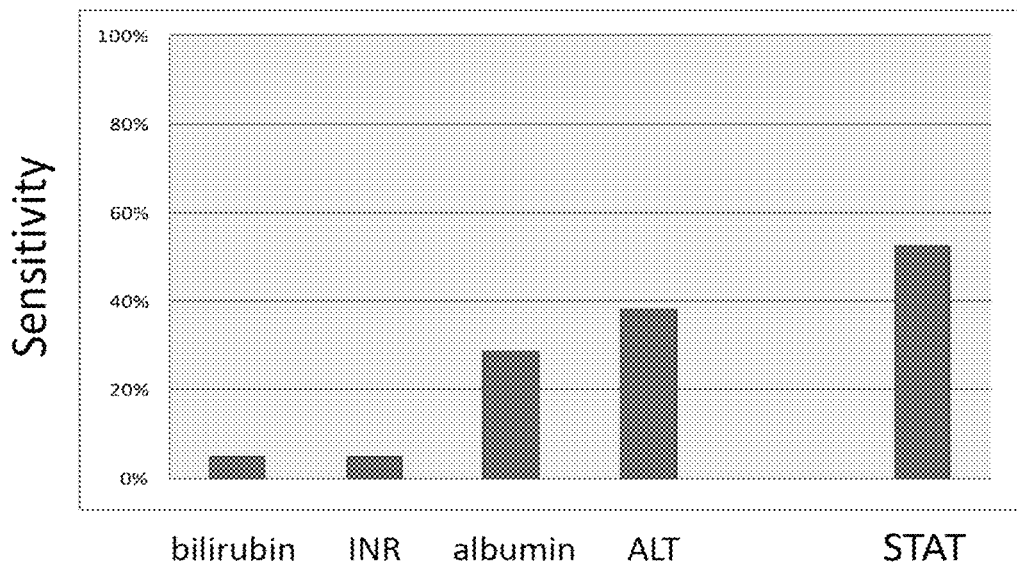
FIG. 9B shows sensitivity of standard lab tests compared to STAT test in detection of early stage chronic HCV patients.
Figure 9C:
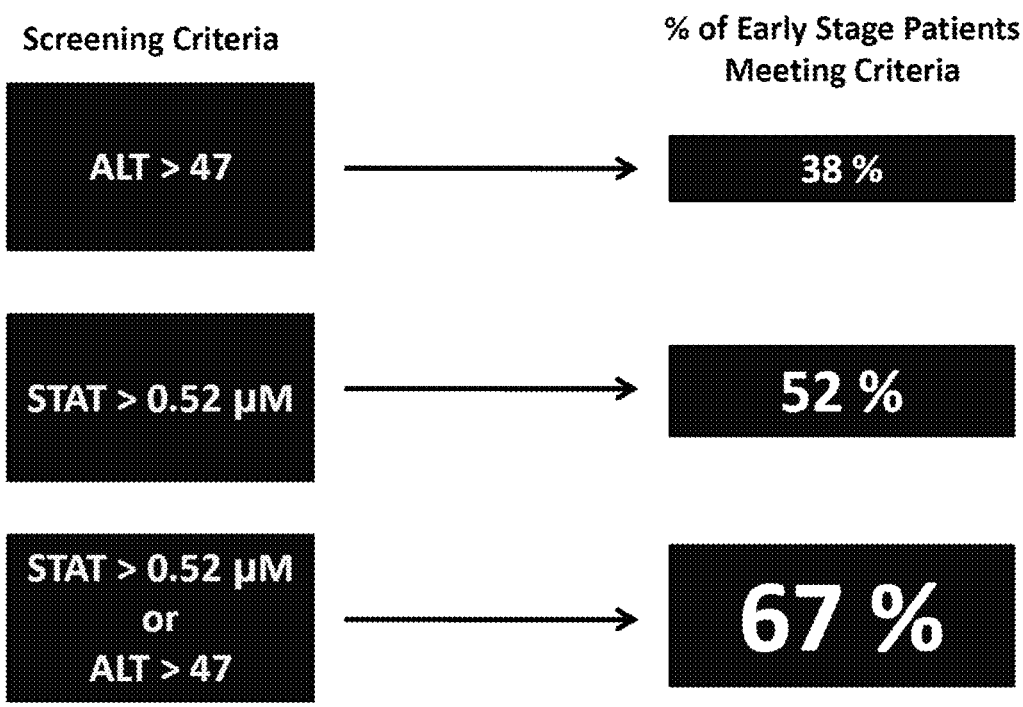
FIG. 9C shows ALT, STAT with cutoffs, and combined screening tests, for identification of early stage HCV patients.

Analytical methods included HPLC (caffeine, antipyrine, MEGX) and spectrophotofluorimetry (galactose). Labeled cholates were assayed by an LCMS method validated to FDA guidelines for accuracy and precision. All were assessed by standard laboratory tests and metabolic tests including caffeine elimination, antipyrine clearance, galactose elimination capacity, and formation of MEGX (monoethylglycinexylidide) metabolite from lidocaine. Most MC Most CHC patients with F0-F2 disease have significant alteration of the portal circulation which can be uniquely quantified by FLOW, SHUNT, and STAT. Differences between controls and HCV F0-F2 patients were evaluated by two-tail unpaired t-tests and is graphically represented as a boxplot in FIG. 9A. The dashed line indicates the mean value. The solid line through the box represents the median value and the bottom and top of each box represent the 25$^{th}$ and 75$^{th}$ percentiles. The error bars represent the 10$^{th}$ and 90$^{th}$ percentiles. ROC analysis of the test results for all subjects was used to determine the optimum cutoffs that distinguished the F0-F2 patients from the controls and that defined hepatic impairment for each test. STAT was analyzed as a screening test in early CHC patients. A comparison of sensitivity in early CHC patients in STAT compared with bilirubin, INR, albumin and ALT is shown in FIG. 9B. The cutoff used to define hepatic impairment and identify the high risk subset in the STAT test is >0.52 uM. Using the cutoff of 0.52 uM, the STAT test identified 52% of early stage patients meeting criteria. When the STAT test was combined with the ALT test, with a cutoff>47, the percentage of early stage HCV patients meeting STAT>0.52 uM or ALT>47 was 67% of early stage patients meeting the criteria; as shown in FIG. 9C. Hepatic impairment may define the subset of F0-F2 patients who have the greatest need for antiviral treatment. STAT is significantly increased in CHC F0-F2 patients. In one aspect, a STAT test result above the high risk cutoff is used to define disease severity or identify patients for further SHUNT and FLOW testing. High SHUNT and low Portal HFR are associated with varices, ascites, other complications, decompensation, and need for transplantation, as further described in Examples 7 and 8.

Example 7. Non-Invasive Measurement of the Portal Circulation Using Cholates Quantifies Disease Severity in Waiting List Patients with Primary Sclerosing Cholangitis MELD (Model for End Stage Liver Disease) was implemented in 2002 to prioritize patients waiting for a liver transplant. MELD is a numerical scale used for adult liver transplant candidates to determine how urgently a patient needs a liver transplant within the next three months. The number is calculated using the most recent lab tests including bilirubin, which measures how efficiently the liver excretes bile; INR (prothrombin time) which measures the ability to make blood clotting factors; and creatinine. MELD may not adequately assess disease severity in listed Primary Sclerosing Cholangitis (PSC) patients compared to dual cholate clearances, or tests which quantify the portal circulation.

The dual cholate clearance method yields 3 test results: Portal-systemic shunt fraction (SHUNT); Portal Hepatic Filtration Rate (Portal HFR, which is also defined as FLOW in above discussions and examples) based on orally administered distinguishable cholate compound in the blood; and Systemic Hepatic Filtration rate (Systemic HFR), based on intravenously administered distinguishable cholate compound in the blood. Cholate-2,2,4,4-$d_4$ (40 mg) is given orally and taken up into the portal vein by specific enteric transporters. Cholate-24-$^{13}$C (20 mg) is given IV and is taken up primarily through the hepatic artery from the systemic circulation. Specific hepatic transporters clear cholate from the portal and systemic circulation.

38 PSC patients were compared to 32 healthy controls. Of the PSC patients, 10 patients were listed for liver transplant; 28 patients were not listed. Peripheral blood samples were collected at 0, 5, 20, 45, 60, and 90 min after simultaneous dosing. Labeled cholates in serum are assayed by LCMS validated to FDA guidelines for accuracy and precision.

In the healthy liver patients, IV clearance and oral cholate clearance curves were used to determine SHUNT: ~20%. The oral cholate clearance per kg body weight was used to determine the Portal Hepatic Filtration Rate (Portal HFR): ~30 mL/min/kg. The IV clearance per kg body weight determines the Systemic HFR~6 mL/min/kg. Healthy controls exhibited low SHUNT, high Portal HFR and high Systemic HFR.

In the diseased liver patients, IV and oral cholate clearance curves were used to determine SHUNT of from about 30% to about 90%. The Portal HFR is from about 20 mL/min/kg to about 2 mL/min/kg. The systemic HFR is from about 4 mL/min/kg to about 1 mL/min/kg. Liver disease patients exhibit higher SHUNT, lower Portal and lower Systemic HFR as disease severity increases.

Results. High SHUNT and low Portal HFR were associated with varices, ascites, other complications, decompensation, and need for transplantation.

FIG. 10 shows (A) Portal HFR determined by oral distinguishable cholate clearance and (B) MELD in PSC patients (n=38) compared to healthy controls (n=32). Portal HFR and SHUNT (not shown) are significantly different in PSC patients vs. healthy controls. FIG. 10 shows (C) Portal HFR determined by oral distinguishable cholate clearance and (D) MELD in PSC patients not listed for liver transplant (n=28) and PSC patients listed for liver transplant (n=10). Portal HFR, SHUNT (not shown) and MELD are significantly different between listed HSC patients and PSC patients not listed for LT. FIG. 10 shows (E) Portal HFR determined by oral distinguishable cholate clearance and (F) MELD in listed PSC patients with varices (n=5) compared to listed PSC patients without varices (n=5). Portal HFR and SHUNT (data not shown), but not MELD, are significantly different between listed PSC patients with and without varices.

Figure 11:
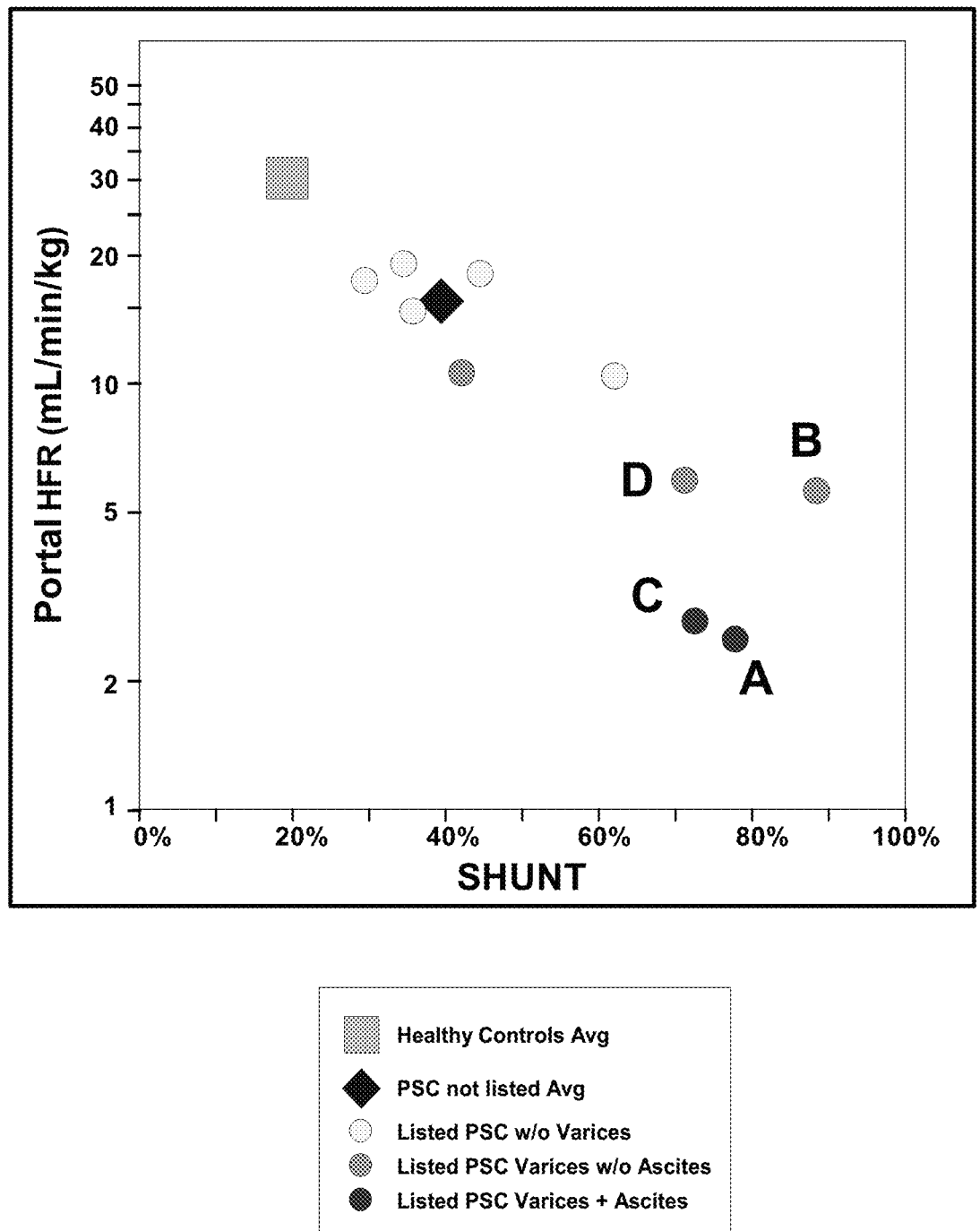
FIG. 11 shows SHUNT and Portal HFR in healthy controls and PSC patients: □ shows avg values for healthy controls; ◊ shows avg PSC patients not listed for LT; open circles ○ show individual listed PSC patients without varices; shaded circles ⊘ show individual listed PSC patients with varices w/o ascites; solid circles ● show individual listed PSC patients with varices and ascites. Also shown are individual values for listed PSC patients A, B, C and D; with varices without ascites (B, D), and with varices and ascites (A, C).

FIG. 11 shows correlation between SHUNT and Portal HFR in healthy controls and PSC patients: □ shows avg values for healthy controls; ◇ shows avg PSC patients not listed for LT; open circles ○ show individual listed PSC patients without varices; shaded grey circles ⊙ show individual listed PSC patients with varices w/o ascites; solid circles ● show individual listed PSC patients with varices and ascites. In addition, individual patients are indicated as follows: Patient A: MELD 20, lowest Portal and lowest Systemic HFR, required emergency LT within one month. Patient B: MELD 17, highest SHUNT, progressing at age 20, was selected to receive LDLT within six months. Patient C: MELD 13, $2^{nd}$ lowest Portal HFR, in 1 yr follow-up; required 6 dilation ERCPs, and paracentesis. Patient D: MELD 11, in 1 yr follow-up had cholecystectomy. Other Patients were found to be clinically stable in 1 yr follow-up. Surprisingly despite relatively low MELD scores, the 4 patients with the highest SHUNT and lowest Portal HFR experienced clinical complications whose severity correlated with cholate testing.

Example 8. Non-Invasive Measurement of the Portal Circulation Using Cholate to Quantify Disease Severity in Primary Sclerosing Cholangitis The hallmark of PSC pathophysiology is portal fibrosis leading to PHTN (portal hypertension) earlier in disease compared to other etiologies of liver disease. The assessment of disease severity in PSC lacks a gold standard, as liver biopsy has significant sampling error and is no longer recommended, HVPG is invasive, expensive and impractical, and clinical models were really created to assess late-stage disease.

There's an unmet need for accurate, noninvasive assessment of PSC over the spectrum of disease severity. Cholate testing was shown to assess disease severity and improve prediction of outcomes in the HCV population.

The objectives of this study were to determine the reproducibility of cholate testing in a PSC cohort, evaluate the ability of cholate testing to quantify disease severity in PSC, and lastly, to explore the prognostic potential of cholate testing to predict clinical decompensation.

Quantitative liver function tests were performed by using two differentially labeled distinguishable cholates administered orally and/or intravenously to yield three different test results: SHUNT, Portal HFR (FLOW) and STAT. Oral cholate is taken up by specific enteric transporters directly into the portal vein and removed by hepatic transporters in its first-pass through the liver. IV cholate distributes systemically and is extracted by both the hepatic artery and portal vein. Concentrations of both cholates were measured at 5 different times within 90 minutes and clearances are calculated. The IV clearance over the oral clearance is the portal-systemic SHUNT fraction. The oral clearance per kilogram of body weight represents the Portal Hepatic Filtration Rate (Portal HFR, FLOW), or amount of portal blood delivery. STAT is the concentration of oral cholate at 60 minutes, and was shown to accurately estimate the portal HFR.

Values for normal liver function were established in healthy controls in previous studies: the average SHUNT is 20%, average HFR (FLOW) is 30, and average STAT is 0.4.

In the diseased liver, as more blood escapes extraction by intra- and extra-hepatic shunting to the systemic circulation, the SHUNT increases (~30-90%), HFR (FLOW) or portal flow decreases (~20 to 2 mL/min/kg), and STAT increases (0.6 to 5 uM).

Methods. Patients underwent History & Physical and standard labs at the baseline visit in addition to cholate testing. A retrospective review of imaging/endoscopic reports, and those with a history decompensation determined by history of ascites or variceal bleeding had ascites on imaging or physical exam, or an endoscopy with evidence of a variceal bleed was conducted. Those with features of PHTN had splenomegaly on radiologic studies or varices documented on endoscopy. Cholate testing was performed 2 different days within a month for reproducibility data, and prospective follow-up was conducted over one year for clinical events.

In total, 38 patients were enrolled in the study, 10 of whom were already listed for transplant. True to typical PSC demographics, almost three-quarters were male, the vast majority were caucasian, mean age was 49. This cohort had relatively mild disease as the meal MELD score was 9.5, mean CTP score was 6 and mean PSC Mayo Risk Score was 0.87. There were 22 patients without features of PHTN, 12 with PHTN without history of decompensation, and 4 with a history of decompensation.

The reproducibility of cholate testing was evaluated by the correlation coefficient, the coefficient of variation, and the intra-class correlation. Cholate testing demonstrated excellent reproducibility with very low variably from one testing date to another. The average CVs for SHUNT, FLOW and STAT were 9.0%, 9.2% and 21%, respectively. As STAT is a single time point measurement, rather than average of several points, a higher CV was expected. There was no significant change in CV across the range of test results indicating excellent reproducibility across wide range of disease severity. The intra-class correlation (ICC), was used to measure variability of an individual over the range of all test results. The ICCs for SHUNT, FLOW and STAT between two test visits were 0.93, 0.91 and 0.96, respectively were, indicating that within individual variability is very low. To put this into context, ICC of 0.7-0.8 indicates strong agreement between tests. All three cholate tests distinguished healthy controls from PSC patients with mild disease, showing the ability to detect subclinical derangements in portal flow.

Figure 12:
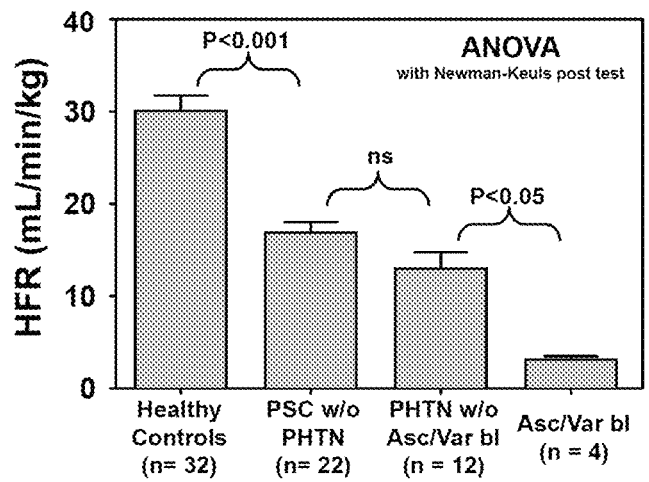
FIG. 12 shows HFR (Portal HFR, FLOW) for PSC patients in various stages of disease compared to healthy controls.

As shown in FIG. 12, Portal HFR distinguished between different degrees of disease severity. Compared to healthy controls, even PSC pts without features of PHTN or evidence of decompensation had significantly impaired HFR. There was also a significant difference between the group with PHTN and the cohort with evidence of decompensation in the form of ascites or variceal bleeding history.

Figure 13:
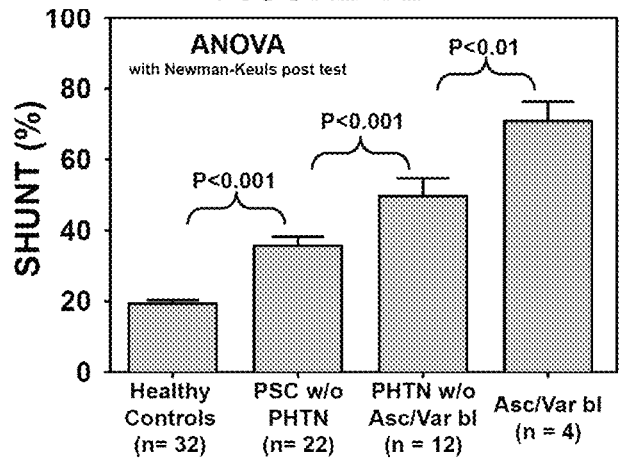
FIG. 13 shows SHUNT for PSC patients in various stages of disease compared to healthy controls.
Figure 14:
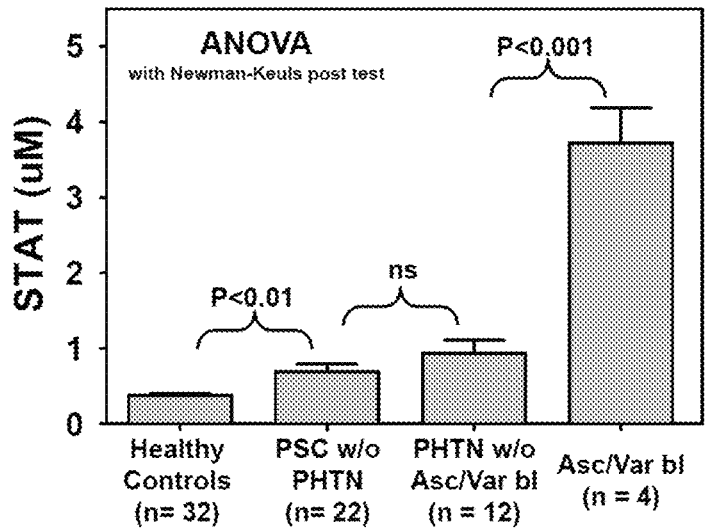
FIG. 14 shows STAT for PSC patients in various stages of disease compared to healthy controls.
Figure 15:
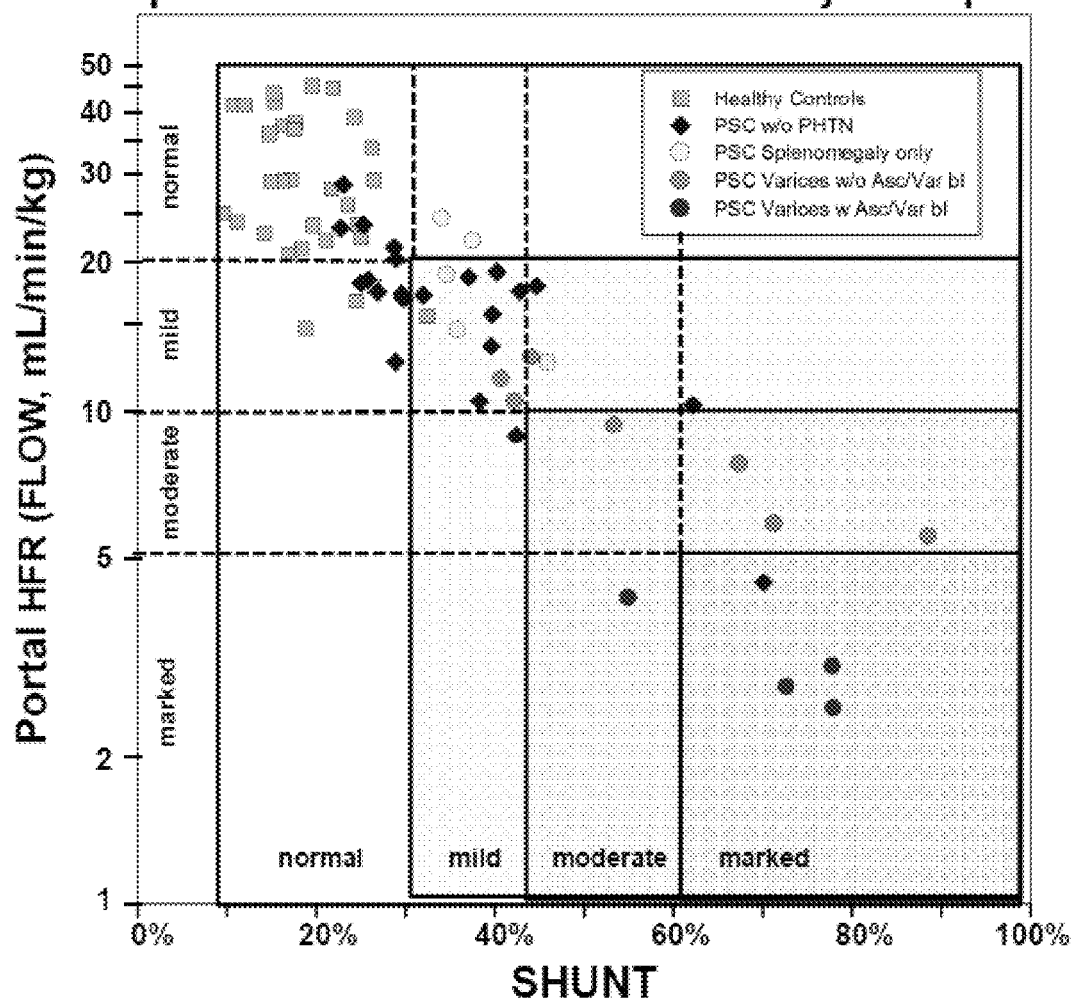
FIG. 15 shows FLOW and SHUNT test results with FLOW and SHUNT cutoff values for individual healthy controls and PSC patients.
Figure 16:
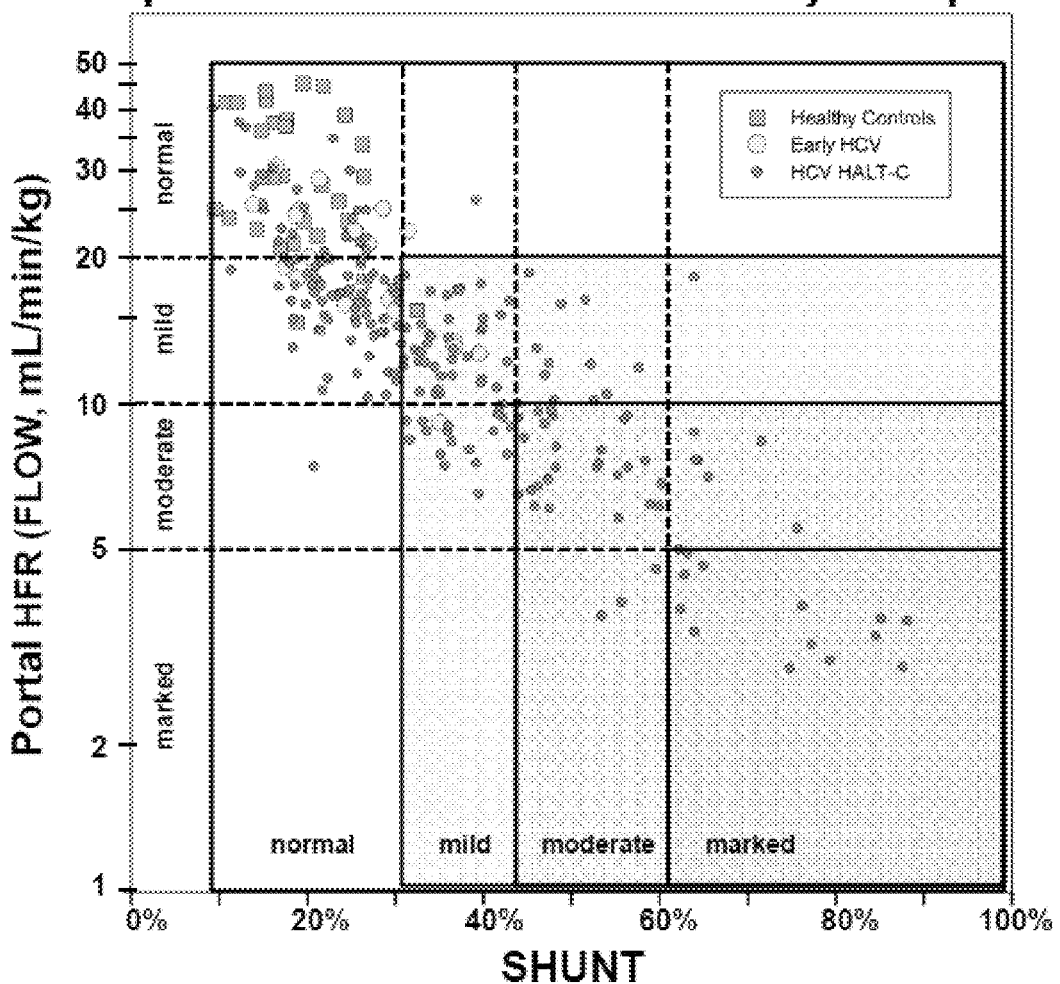
FIG. 16 shows FLOW and SHUNT test results with FLOW and SHUNT cutoff values for individual healthy controls and HCV patients.

As shown in FIG. 13, SHUNT demonstrated significant differences between each subgroup, again distinguishing PSC patients with mild disease from healthy controls, and also differentiating the cohorts with and without PHTN, and the group with PHTN from that with history of ascites or variceal bleeding.

FIG. 14 illustrates that, surprisingly, with a single blood sample drawn at a specific time point, STAT showed significant differences between healthy controls and mild disease, and those with PHTN and decompensation.

Each of the three cholate tests showed a significant association with varices. ROC curve analysis of SHUNT, FLOW and STAT tests was used to identify PSC Patients with varices (10 of 35). AUROC (area under the receiver operating characteristic curve) was used to derive the C statistic. A STAT cutoff above 0.79 uM resulted in sensitivity of 100% and specificity of 84% for predicting varices as shown in the Table 9.

TABLE 9

Cutoff Values in PSC Patients for SHUNT, FLOW and STAT Predictive of Varices.

| Cutoff values | Sensitivity | Specificity | PPV | NPV | C-statistic |
|---|---|---|---|---|---|
| SHUNT >40.5% | 100% | 76% | 63% | 100% | 0.92 |
| FLOW <13 mL/min/kg | 100% | 76% | 63% | 100% | 0.93 |
| STAT >0.79 uM | 100% | 84% | 71% | 100% | 0.93 |

ROC curve analysis of SHUNT, FLOW, and STAT tests was used to identify PSC patients with decompensation (history of variceal bleed or ascites, 4 of 35). A STAT cutoff above 2.2 uM resulted in sensitivity of 100% and specificity of 97% for predicting decompensation as shown in the Table 10.

TABLE 10

Cutoff Values in PSC Patients for SHUNT, FLOW and STAT Predictive of Decompensation.

| Cutoff values | Sensitivity | Specificity | PPV | NPV | C-statistic |
|---|---|---|---|---|---|
| SHUNT >54% | 100% | 87% | 50% | 100% | 0.94 |
| FLOW <4.3 mL/min/kg | 100% | 100% | 100% | 100% | 1.00 |
| STAT >2.2 uM | 100% | 97% | 80% | 100% | 0.99 |

SHUNT, FLOW and STAT tests can be used to predict the presence of varices and inform which patients should have endoscopic evaluation, and may predict clinical decompensation more accurately than traditional clinical models. SHUNT, FLOW, and STAT tests were determined to be reproducible, reliable diagnostic tests to assess PSC disease across the spectrum of severity.

SHUNT, FLOW, STAT and PSC Disease Severity

A scale of PSC Disease Severity Cutoff Values for the SHUNT, FLOW and STAT tests was established by the methods above and is shown in Table 11.

TABLE 11

Cutoff Values in PSC Patients for SHUNT, FLOW and STAT Predictive of Disease Severity.

| SHUNT (%) | FLOW (mL min$^{-1}$kg$^{-1}$) | STAT (µM) | PSC Disease Severity |
|---|---|---|---|
| 71 ± 11 | 3 ± 1 | 3.7 ± 0.9 | PSC decompensated (variceal bleeding or ascites) |
| 62 ± 17 | 7 ± 4 | 2.2 ± 1.4 | PSC w Varices |
| 54 ± 19 | 11 ± 7 | 1.6 ± 1.5 | PSC w PHTN (splenography or varices) |
| 37 ± 12 | 16 ± 5 | 0.7 ± 0.5 | PSC w/o PHTN |
| 19 ± 5 | 30 ± 9 | 0.4 ± 0.1 | Healthy |

REFERENCES

1. Browning, J D, Szczepaniak, L S, Dobbins, R, Nuremberg, P, Horton, J D, Cohen, J C, Grundy, S M and Hobbs, H H. 2004. Prevalence of hepatic steatosis in an urban population in the united states: Impact of ethnicity. Hepatology. 40: 1387-1395.
2. Adams, L A, Lymp, J F, St Sauver, J, Sanderson, S O, Lindor, K D, Feldstein, A and Angulo, P. 2005. The natural history of nonalcoholic fatty liver disease: A population-based cohort study. Gastroenterology. 129: 113-121.
3. Janes, C H and Lindor, K D. 1993. Outcome of patients hospitalized for complications after outpatient liver biopsy. Ann Intern Med. 118: 96-98.
4. Seeff, L B, Everson, G T, Morgan, T R, Curto, T M, Lee, W M, Ghany, M G, Shiffman, M L, Fontana, R J, Di Bisceglie, A M, Bonkovsky, H L and Dienstag, J L. 2010. Complication rate of percutaneous liver biopsies among persons with advanced chronic liver disease in the halt-c trial. Clin Gastroenterol Hepatol. 8: 877-883.
5. Vuppalanchi, R, Unalp, A, Van Natta, M L, Cummings, O W, Sandrasegaran, K E, Hameed, T, Tonascia, J and Chalasani, N. 2009. Effects of liver biopsy sample length and number of readings on sampling variability in non-alcoholic fatty liver disease. Clin Gastroenterol Hepatol. 7: 481-486.
6. Bedossa, P, Dargere, D and Paradis, V. 2003. Sampling variability of liver fibrosis in chronic hepatitis c. Hepatology. 38: 1449-1457.
7. Regev, A, Berho, M, Jeffers, L J, Milikowski, C, Molina, E G, Pyrsopoulos, N T, Feng, Z Z, Reddy, K R and Schiff, E R. 2002. Sampling error and intraobserver variation in liver biopsy in patients with chronic hcv infection. Am J Gastroenterol. 97: 2614-2618.
8. Rousselet, M C, Michalak, S, Dupre, F, Croue, A, Bedossa, P, Saint-Andre, J P and Cales, P. 2005. Sources of variability in histological scoring of chronic viral hepatitis. Hepatology. 41: 257-264.
9. Ishak, K, Baptista, A, Bianchi, L, Callea, F, De Groote, J, Gudat, F, Denk, H, Desmet, V, Korb, G, MacSween, R N and et al. 1995. Histological grading and staging of chronic hepatitis. J Hepatol. 22: 696-699.
10. Knodell, R G, Ishak, K G, Black, W C, Chen, T S, Craig, R, Kaplowitz, N, Kiernan, T W and Wollman, J. 1981. Formulation and application of a numerical scoring system for assessing histological activity in asymptomatic chronic active hepatitis. Hepatology. 1: 431-435.
11. Batts, K P and Ludwig, J. 1995. Chronic hepatitis. An update on terminology and reporting. Am J Surg Pathol. 19: 1409-1417.
12. Scheuer, P J. 1991. Classification of chronic viral hepatitis: A need for reassessment. J Hepatol. 13: 372-374.
13. Group, TFMCS. 1994. Intraobserver and interobserver variations in liver biopsy interpretation in patients with chronic hepatitis c Hepatology. 20: 15-20.
14. Brunt, E M, Janney, C G, Di Bisceglie, A M, Neuschwander-Tetri, B A and Bacon, B R. 1999. Nonalcoholic steatohepatitis: A proposal for grading and staging the histological lesions. Am J Gastroenterol. 94: 2467-2474.
15. Kleiner, D E, Brunt, E M, Van Natta, M, Behling, C, Contos, M J, Cummings, O W, Ferrell, L D, Liu, Y C, Torbenson, M S, Unalp-Arida, A, Yeh, M, McCullough, A J and Sanyal, A J. 2005. Design and validation of a histological scoring system for nonalcoholic fatty liver disease. Hepatology. 41: 1313-1321.
16. Ratziu, V, Charlotte, F, Heurtier, A, Gombert, S, Giral, P, Bruckert, E, Grimaldi, A, Capron, F and Poynard, T. 2005. Sampling variability of liver biopsy in nonalcoholic fatty liver disease. Gastroenterology. 128: 1898-1906.
17. Everson, G T, Shiffman, M L, Morgan, T R, Hoefs, J C, Sterling, R K, Wagner, D A, Kulig, C C, Curto, T M and Wright, E C. 2008. The spectrum of hepatic functional impairment in compensated chronic hepatitis c: Results from the hepatitis c anti-viral long-term treatment against cirrhosis trial. Aliment Pharmacol Ther. 27: 798-809.
18. Everson, G T, Martucci, M A, Shiffman, M L, Sterling, R K, Morgan, T R and Hoefs, J C. 2007. Portal-systemic shunting in patients with fibrosis or cirrhosis due to chronic hepatitis c: The minimal model for measuring cholate clearances and shunt. Aliment Pharmacol Ther. 26: 401-410.
19. Everson, G T, Shiffman, M L, Hoefs, J C, Morgan, T R, Sterling, R K, Wagner, D A, Desanto, J L, Curto, T M and Wright, E C. 2009. Quantitative tests of liver function measure hepatic improvement after sustained virological response: Results from the halt-c trial. Aliment Pharmacol Ther. 29: 589-601.
20. Wilson, S and Chalasani, N. 2007. Noninvasive markers of advanced histology in nonalcoholic fatty liver disease: Are we there yet? Gastroenterology. 133: 1377-1378; discussion 1378-1379.
21. Vuppalanchi, R and Chalasani, N. 2009. Nonalcoholic fatty liver disease and nonalcoholic steatohepatitis: Selected practical issues in their evaluation and management. Hepatology. 49: 306-317.
22. Soderberg, C, Stal, P, Askling, J, Glaumann, H, Lindberg, G, Marmur, J and Hultcrantz, R. 2010. Decreased survival of subjects with elevated liver function tests during a 28-year follow-up. Hepatology. 51: 595-602.
23. Rafiq, N, Bai, C, Fang, Y, Srishord, M, McCullough, A, Gramlich, T and Younossi, Z M. 2009. Long-term follow-up of patients with nonalcoholic fatty liver. Clin Gastroenterol Hepatol. 7: 234-238.
24. Angulo, P. 2010. Long-term mortality in nonalcoholic fatty liver disease: Is liver histology of any prognostic significance? Hepatology. 51: 373-375.
25. Mukherjee, S and Sorrell, M F. 2006. Noninvasive tests for liver fibrosis. Semin Liver Dis. 26: 337-347.
26. Shah, A G, Lydecker, A, Murray, K, Tetri, B N, Contos, M J and Sanyal, A J. 2009. Comparison of noninvasive markers of fibrosis in patients with nonalcoholic fatty liver disease. Clin Gastroenterol Hepatol. 7: 1104-1112.
27. Boursier, J, Bacq, Y, Halfon, P, Leroy, V, de Ledinghen, V, de Muret, A, Bourliere, M, Sturm, N, Foucher, J, Oberti, F, Rousselet, M C and Cales, P. 2009. Improved diagnostic accuracy of blood tests for severe fibrosis and cirrhosis in chronic hepatitis c. Eur J Gastroenterol Hepatol. 21: 28-38.
28. Shaheen, A A, Wan, A F and Myers, R P. 2007. Fibrotest and fibroscan for the prediction of hepatitis c-related fibrosis: A systematic review of diagnostic test accuracy. Am J Gastroenterol. 102: 2589-2600.
29. Ratziu, V, Massard, J, Charlotte, F, Messous, D, Imbert-Bismut, F, Bonyhay, L, Tahiri, M, Munteanu, M, Thabut, D, Cadranel, J F, Le Bail, B, de Ledinghen, V and Poynard, T. 2006. Diagnostic value of biochemical markers (fibrotest-fibrosure) for the prediction of liver fibrosis in patients with non-alcoholic fatty liver disease. BMC Gastroenterol. 6: 6.
30. Angulo, P, Hui, J M, Marchesini, G, Bugianesi, E, George, J, Farrell, G C, Enders, F, Saksena, S, Burt, A D, Bida, J P, Lindor, K, Sanderson, S O, Lenzi, M, Adams, L A, Kench, J, Therneau, T M and Day, C P. 2007. The nafld fibrosis score: A noninvasive system that identifies liver fibrosis in patients with nafld. Hepatology. 45: 846-854.
31. Wong, V W, Vergniol, J, Wong, G L, Foucher, J, Chan, H L, Le Bail, B, Choi, P C, Kowo, M, Chan, A W, Merrouche, W, Sung, J J and de Ledinghen, V. 2010. Diagnosis of fibrosis and cirrhosis using liver stiffness measurement in nonalcoholic fatty liver disease. Hepatology. 51: 454-462.
32. Braden, B, Faust, D, Sarrazin, U, Zeuzem, S, Dietrich, C F, Caspary, W F and Sarrazin, C. 2005. 13c-methacetin breath test as liver function test in patients with chronic hepatitis c virus infection. Aliment Pharmacol Ther. 21: 179-185.
33. Del Poggio, P and Colombo, S. 2009. Is transient elastography a useful tool for screening liver disease? World J Gastroenterol. 15: 1409-1414.
34. Friedrich-Rust, M, Ong, M F, Martens, S, Sarrazin, C, Bojunga, J, Zeuzem, S and Herrmann, E. 2008. Performance of transient elastography for the staging of liver fibrosis: A meta-analysis. Gastroenterology. 134: 960-974.
35. Rossi, E, Adams, L, Prins, A, Bulsara, M, de Boer, B, Garas, G, MacQuillan, G, Speers, D and Jeffrey, G. 2003. Validation of the fibrotest biochemical markers score in assessing liver fibrosis in hepatitis c patients. Clin Chem. 49: 450-454.
36. Trauner, M and Boyer, J L. 2003. Bile salt transporters: Molecular characterization, function, and regulation. Physiol Rev. 83: 633-671.
37. Manning, D S and Afdhal, N H. 2008. Diagnosis and quantitation of fibrosis. Gastroenterology. 134: 1670-1681.
38. Poynard, T, Ingiliz, P, Elkrief, L, Munteanu, M, Lebray, P, Morra, R, Messous, D, Bismut, F I, Roulot, D, Benhamou, Y, Thabut, D and Ratziu, V. 2008. Concordance in a world without a gold standard: A new non-invasive methodology for improving accuracy of fibrosis markers. PLoS One. 3: e3857.
39. Goodman, Z D. 2007. Grading and staging systems for inflammation and fibrosis in chronic liver diseases. J Hepatol. 47: 598-607.
40. Ludwig, J, Barham, S S, LaRusso, N F, Elveback, L R, Wiesner, R H and McCall, J T. 1981. Morphologic features of chronic hepatitis associated with primary sclerosing cholangitis and chronic ulcerative colitis. Hepatology. 1: 632-640.

We claim:

1. A method of risk assessment for determining liver disease severity, disease progression, stage of disease, disease prognosis, fibrosis stage, and/or response to treatment in a patient having, suspected of having, or at risk of having a chronic liver disease, comprising
    receiving a sample consisting of a single blood or serum sample from the patient obtained at a single, specific time point less than 3 hours after oral administration of a single distinguishable agent to the patient, wherein no other distinguishable agent is intravenously co-administered, wherein the distinguishable agent is capable of exhibiting hepatic extraction of at least 60% in first pass through the liver of a healthy subject following oral administration, and wherein the distinguishable agent is a distinguishable bile acid or bile acid conjugate;
    measuring the concentration of the distinguishable agent in the sample, wherein the measuring comprises quantifying the concentration of the distinguishable agent in the sample by GC-MS, LC-MS, scintillation spectroscopy, autoanalyzer, luminescence, or ELISA; and
    comparing the concentration of the distinguishable agent in the sample to a cutoff value or cutoffs of values from a known patient population(s), and/or to the concentration of the distinguishable agent in one or more earlier samples from the same patient over time, wherein the concentration of distinguishable agent in the sample compared to the cutoff value or cutoffs of values from a known patient population(s), and/or to the concentration of the distinguishable agent in one or more earlier samples from the same patient over time is an estimation of portal blood flow in the patient.

2. The method of claim 1, wherein an increase in the concentration of the distinguishable agent in the sample compared to one or more earlier samples from the same patient over time indicates liver disease progression in the patient, the method further comprising
    additional testing selected from the group consisting of an additional liver function test and an additional clinical screening procedure.

3. The method of claim 2, wherein the additional clinical screening procedure is selected from the group consisting of liver biopsy, histological assessment, endoscopy, radiologic imaging, elastography, biomarker panel, metabolic test, Model for End Stage Liver Disease (MELD) score, Childs-Turcotte-Pugh (CTP) score, fibrosis test, and hepatocellular carcinoma (HCC) screening.

4. The method of claim 1, further comprising
    assigning the concentration of the distinguishable agent in the patient sample to one of a multiplicity of ranges defined by the cutoff value or cutoffs of values from the known patient population(s) to obtain a test result, said multiplicity of ranges comprising at least two ranges comprising a range below a first cutoff value, and a range above a second cutoff value.

5. The method of claim 4, wherein the liver disease is selected from the group consisting of chronic hepatitis C; chronic hepatitis B; cytomegalovirus; Epstein Barr virus; primary sclerosing cholangitis (PSC); alcoholic liver disease; drug toxicity; autoimmune liver disease; primary biliary cirrhosis; cryptogenic cirrhosis; hemochromatosis; Wilson's disease; alpha-1-antitrypsin deficiency; cholestatic liver disease; hepatocellular carcinoma (HCC); and non-alcoholic fatty liver disease (NAFLD).

6. The method of claim 5, wherein the test result differentiates stage of non-alcoholic fatty liver disease (NAFLD) into simple fatty liver (hepatic steatosis) and non-alcoholic steatohepatitis (NASH), and or is predictive of fibrosis score, presence or absence of varices, cirrhosis, and clinical decompensation.

7. The method of claim 5, wherein the drug toxicity is selected from the group consisting of methotrexate toxicity, amiodarone toxicity, and nitrofurantoin toxicity.

8. The method of claim 4, wherein the first cutoff value and the second cutoff value are different, and one or more intermediate ranges are between the first and second cutoff values.

9. The method of claim 4, wherein the first cutoff value and the second cutoff value are the same.

10. The method of claim 1, wherein the treatment is selected from the group consisting of lifestyle modification; diet modification; antiviral treatment; pharmacotherapy; treatment of portal hypertension; hepatic resection; and liver transplantation.

11. The method of claim 1, wherein the orally administered distinguishable agent is capable of exhibiting hepatic extraction of at least about 80% in first pass through the liver of a healthy subject following oral administration.

12. The method of claim 1, wherein the distinguishable agent is a distinguishable bile acid.

13. The method of claim 12, wherein the distinguishable bile acid is a distinguishable cholate, deoxycholate, lithocholate, or chenodeoxycholate compound.

14. The method of claim 13, wherein the distinguishable cholate compound is an isotopically labeled cholic acid.

15. The method of claim 14, wherein the isotopically labeled cholic acid is a stable isotope labeled cholic acid.

16. The method of claim 15, wherein the stable isotope labeled cholic acid is selected from $24\text{-}^{13}C$ cholic acid or $2,2,4,4\text{-}H^2H$ cholic acid.

17. The method of claim 1, wherein the single blood or serum sample is collected at one time point selected from about 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 minutes, or any time point in between, after oral administration of the distinguishable agent.

18. The method of claim 17, wherein the single blood or serum sample is collected at one time point selected from about 45, about 60 or about 90 minutes after oral administration of the distinguishable agent.

19. The method of claim 18, wherein the single blood or serum sample is collected at about 60 minutes after oral administration of the distinguishable agent.

20. The method of claim 1, wherein the method further comprises estimating portal hepatic filtration rate (portal HFR) in the patient comprising:
converting the concentration of the distinguishable agent in the sample (μM) by using an equation into an estimated portal HFR (mL/min/kg) in the patient; and
comparing the estimated portal HFR in the patient to a portal HFR (FLOW) cutoff value or cutoffs of values established from known patient population or to a previous estimated portal HFR (mL/min/kg) in the patient over time to assess liver disease severity, disease progression, and/or response to treatment in the patient.

21. The method of claim 20, wherein a decrease in estimated portal HFR in the patient over lime is indicative of liver disease progression.

* * * * *